US008715670B2

(12) United States Patent
Lee et al.

(10) Patent No.: US 8,715,670 B2
(45) Date of Patent: May 6, 2014

(54) HUMAN MONOCLONAL ANTIBODY THAT SPECIFICALLY BINDS TO VCAM-1 AND A COMPOSITION FOR TREATING AN INFLAMMATORY DISEASE OR A CANCER COMPRISING THE SAME

(75) Inventors: Jung Tae Lee, Daejeon (KR); Kyung Duk Moon, Daejeon (KR); Ji Yong Yoon, Daejeon (KR); Byung Je Sung, Daejeon (KR); Dong Heon Lee, Daejeon (KR); Il Sun Lee, Daejeon (KR); Dong Eun Lee, Busan (KR); Su Yeon Ryu, Daejeon (KR); Young Woo Park, Daejeon (KR); So Young Choi, Daejeon (KR); Ji Hyun Park, Gyeongsangnam-do (KR); Myeoung Hee Jang, Daejeon (KR)

(73) Assignee: Hanwha Chemical Corporation, Seoul (KR)

( * ) Notice: Subject to any disclaimer, the term of this patent is extended or adjusted under 35 U.S.C. 154(b) by 0 days.

(21) Appl. No.: 13/262,212

(22) PCT Filed: Mar. 31, 2010

(86) PCT No.: PCT/KR2010/001988
§ 371 (c)(1),
(2), (4) Date: Apr. 4, 2012

(87) PCT Pub. No.: WO2010/114312
PCT Pub. Date: Oct. 7, 2010

(65) Prior Publication Data
US 2012/0308574 A1    Dec. 6, 2012

(30) Foreign Application Priority Data
Mar. 31, 2009    (KR) ........................ 10-2009-0027721

(51) Int. Cl.
*A61K 39/395*    (2006.01)
*C07K 16/28*    (2006.01)
*G01N 33/53*    (2006.01)

(52) U.S. Cl.
USPC .................. 424/152.1; 424/130.1; 424/133.1; 424/142.1; 424/141.1; 424/143.1; 435/7.1; 435/7.2; 435/7.21; 530/387.1; 530/387.3; 530/388.1; 530/388.15; 530/388.2; 530/388.22

(58) Field of Classification Search
None
See application file for complete search history.

(56) References Cited

U.S. PATENT DOCUMENTS

2010/0172902 A1*    7/2010    Chung et al. ............... 424/133.1
2010/0183599 A1*    7/2010    Mundy et al. .............. 424/133.1

FOREIGN PATENT DOCUMENTS

| CN | 1321091 A | 11/2001 |
|---|---|---|
| WO | WO 93/14220 | 7/1993 |
| WO | WO 00/15247 | 3/2000 |
| WO | WO 2007/139359 | 12/2007 |

OTHER PUBLICATIONS

International Search Report for PCT/KR2010/001988, mailed on Jan. 21, 2011.
Written Opinion for PCT/KR2010/001988, mailed on Jan. 21, 2011.
Chuluyan et al., "Domains 1 and 4 of Vascular Cell Adhesion Molecule-1 (CD106) Both Support Very Late Activation Antigen-4 (CD49d/CD29)-Dependent Monocyte Transendothelial Migration," *Journal of Immunology*, 155:3135-3144 (1995).
Larbi et al., "VCAM-1 has a tissue-specific role in mediating interleukin-4-induced eosinophil accumulation in rat models: evidence for a dissociation between endothelial-cell VCAM-1 expression and a functional role in eosinophil migration," *Blood*, 96(10):3601-3609 (2000).
Mueller et al., "Humanized Porcine VCAM-Specific Monoclonal Antibodies with Chimeric IgG2/G4 Constant Regions Block Human Leukocyte Binding to Porcine Endothelial Cells," *Molecular Immunology*, 34(6):441-452 (1997).
Van Wetering et al., "VCAM-1mediated Rac signaling controls endothelial cell-cell contacts and leukocyte transmigration," *Am J Phsiol Cell Physiol*, 285:C343-C352 (2003).
Wang et al., "The crystal structure of an N-terminal two-domain fragment of vascular cell adhesion molecule 1 (VCAM-1): A cyclic peptide based on the domain 1 C-D loop can inhibit VCAM-1-α4 integrin interaction," *Proc. Natl. Acad. Sci. USA*, 92:5714-5718 (1995).
Carlos et al., "Vascular Cell Adhesion Molecule-1 Mediates Lymphocyte Adherence to Cytokine-Activated Cultured Human Endothelial Cells," Blood 76(5) 965-970, Sep. 1, 1990.
Miyake et al., "A VCAM-like Adhesion Molecule on Murine Bone Marrow Stromal Cells Mediates Binding of Lymphocyte Precursors in Culture," The Journal of Cell Biology 114(3): 557-565, Aug. 1991.
Slack-Davis et al., "Vascular Cell Adhesion Molecule-1 Is a Regulator of Ovarian Cancer Peitoneal Metastasis," Cancer Res. 69(4): 1469-1476, Feb. 15, 2009.
State Intellectual Property Office of PRC, Notification of First Office Action (PCT), Application No. 201080014771.6, Applicant: Hanwha Chemical Corporation, Date of Issue: May 31, 2013, English Translation and original Chinese Language Office Action, 11 pages.
Rothe et al., "The Human Combinatorial Antibody Library HuCAL Gold Combines Diversification of All Six CDRs According to the Natural Immune System with a Novel Display Method for Efficient Selection of High-Affinity Antibodies," J. Mol. Biol. 376: 1182-1200, Feb. 2008.
Rauchenberger et al., "Human Combinatorial Fab Library Yielding Specific and Functional Antibodies against the Human Fibroblast Growth Factor Receptor 3," The Journal of Biological Chemistry 278(40): 38194-38205, Oct. 2003.

* cited by examiner

*Primary Examiner* — Phillip Gambel
(74) *Attorney, Agent, or Firm* — Cooley LLP

(57) ABSTRACT

The present invention relates to a human monoclonal antibody that specifically binds to VCAM-1, and a therapeutic composition for the treatment of inflammatory disease or cancer comprising the same. The human monoclonal antibody according to the present invention shows a strong affinity to VCAM-1 expressed on human or mouse endothelial cell, effectively inhibits leukocyte adhesion to activated endothelial cells expressing VCAM-1, and shows a low immunogenicity, thereby being used for the treatment of cancer or inflammatory disease such as asthma, rhinitis, arthritis, multiple sclerosis, bowel disease, arteriosclerosis, myocardial infarction and transplant rejection.

17 Claims, 7 Drawing Sheets

Figure 2

VH Sequence

| Clone Name | Frame 1 | CDR 1 | Frame 2 | CDR 2 | Frame 3 | CDR 3 | Frame 4 |
|---|---|---|---|---|---|---|---|
| 4B (SEQ ID NO. 1) | QMQLVESGGGLVQPGGSLRLSCAASGFTFS | SYGVS (SEQ ID NO. 2) | WVRQAPGKGLEWVS | RISGSGGSTYYADSVKG (SEQ ID NO. 3) | RFTISRDNSKSTLYLQMNSLRAEDTAVYYCAR | PIFYGGNSAFDS (SEQ ID NO. 4) | WGQGTLVTVSS |
| 7C (SEQ ID NO. 5) | QVQLVESGGGVVQPGGSLRLSCAASGFTFD | DYAMH (SEQ ID NO. 6) | WVRQAPGKGLEWVS | LISGDGTDTYYADSVKG (SEQ ID NO. 7) | RFTISRDNSKNSLYLQMNSLRAEDTAVYYCAK | RGYSIYLGALDG (SEQ ID NO. 8) | WGQGTKITVSS |
| 7H (SEQ ID NO. 9) | QMQLVQSGGDLVKPGGESLRLSCAASGFTFN | DAWMT (SEQ ID NO. 10) | WVRQPPGKGLEWVG | RIKSTTDGGTTNYAAPVEG (SEQ ID NO. 11) | RFTISRDDSRQNTLVLEMNSLRAEDTAVYYCAR | IPLENHDSGGYHCAFDI (SEQ ID NO. 12) | WGQGTMVTVSS |

VL Sequence

| Clone Name | Frame 1 | CDR 1 | Frame 2 | CDR 2 | Frame 3 | CDR 3 | Frame 4 |
|---|---|---|---|---|---|---|---|
| 4B (SEQ ID NO. 13) | QLVLTQPPSVSAAPGQKVTISC | SGSSSNIGNNFVS (SEQ ID NO. 14) | WYQHLPGTAPKLLIY | DNNKRPS (SEQ ID NO. 15) | GIPDRFSGSKSGTSATLGAGLQTGDDADYYC | GTWDSSLSAVV (SEQ ID NO. 16) | FGTGAKVTVL |
| 7C (SEQ ID NO. 17) | QLVLTQSFSVSVAPGQTARITC | GGDNIGRESVH (SEQ ID NO. 18) | WYQQKAGQAPVLVIY | YDSDRPS (SEQ ID NO. 19) | GIPERFSGGSNSGNTATLTISWDAGDEADYYC | QVWDSSSDHVV (SEQ ID NO. 20) | FGGGTKLTVL |
| 7H (SEQ ID NO. 21) | DIQMTQSPFSSLAVSLGERATINC | KSSQSVLYSSNNKNYLA (SEQ ID NO. 22) | WYQQKPGQPPKLLIY | WASTRES (SEQ ID NO. 23) | GVPDRFSGSGSGTDFTLTISSLQPEDFASYYC | QESYSAPYT (SEQ ID NO. 24) | FGQGTKVEKR |

Figure 3

SEQUENCE LISTING

<160> NUMBER OF SEQ ID NOS: 38

<210> SEQ ID NO 1
<211> LENGTH: 121
<212> TYPE: PRT
<213> ORGANISM: Artificial Sequence
<220> FEATURE:
<223> OTHER INFORMATION: a heavy chain variable region

<400> SEQUENCE: 1

```
Gln Met Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Val Ser Trp Val Arg Gln Ala Pro Gly Lys Gly Leu Glu Trp Val
         35                  40                  45

Ser Arg Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Ser Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Ile Phe Tyr Gly Gly Asn Ser Ala Phe Asp Ser Trp Gly
            100                 105                 110

Gln Gly Thr Leu Val Thr Val Ser Ser
        115                 120
```

<210> SEQ ID NO 2
<211> LENGTH: 5
<212> TYPE: PRT
<213> ORGANISM: Artificial Sequence
<220> FEATURE:
<223> OTHER INFORMATION: CDR1 of a heavy chain variable region

<400> SEQUENCE: 2

Ser Tyr Gly Val Ser
 1               5

<210> SEQ ID NO 3
<211> LENGTH: 17
<212> TYPE: PRT
<213> ORGANISM: Artificial Sequence
<220> FEATURE:
<223> OTHER INFORMATION: CDR2 of a heavy chain variable region

<400> SEQUENCE: 3

Arg Ile Ser Gly Ser Gly Gly Ser Thr Tyr Tyr Ala Asp Ser Val Lys
 1               5                  10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: CDR3 of a heavy chain variable region

<400> SEQUENCE: 4

Pro Ile Phe Tyr Gly Gly Asn Ser Ala Phe Asp Ser
 1               5                  10

<210> SEQ ID NO 5
<211> LENGTH: 120
<212> TYPE: PRT
<213> ORGANISM: Artificial Sequence
<220> FEATURE:
<223> OTHER INFORMATION: a heavy chain variable region

<400> SEQUENCE: 5

Gln Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Gly Asp Gly Thr Asp Thr Tyr Tyr Ala Asp Ser Val
        50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Arg Gly Tyr Ser Tyr Leu Gly Ala Leu Asp Gly Trp Gly Gln
            100                 105                 110

Gly Thr Lys Ile Thr Val Ser Ser
        115                 120

<210> SEQ ID NO 6
<211> LENGTH: 5

```
<212> TYPE: PRT
<213> ORGANISM: Artificial Sequence
<220> FEATURE:
<223> OTHER INFORMATION: CDR1 of a heavy chain variable region

<400> SEQUENCE: 6

Asp Tyr Ala Met His
 1               5

<210> SEQ ID NO 7
<211> LENGTH: 17
<212> TYPE: PRT
<213> ORGANISM: Artificial Sequence
<220> FEATURE:
<223> OTHER INFORMATION: CDR2 of a heavy chain variable region

<400> SEQUENCE: 7

Leu Ile Ser Gly Asp Gly Thr Asp Thr Tyr Tyr Ala Asp Ser Val Lys
 1               5                  10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: CDR3 of a heavy chain variable region

<400> SEQUENCE: 8

Arg Gly Tyr Ser Tyr Leu Gly Ala Leu Asp Gly
 1               5                  10

<210> SEQ ID NO 9
<211> LENGTH: 128
<212> TYPE: PRT
<213> ORGANISM: Artificial Sequence
<220> FEATURE:
<223> OTHER INFORMATION: a heavy chain variable region

<400> SEQUENCE: 9

Gln Met Gln Leu Val Gln Ser Gly Gly Asp Leu Val Lys Pro Gly Glu
 1               5                  10                  15

Ser Leu Arg Leu Ser Cys Ala Ala Ser Gly Phe Thr Phe Asn Asp Ala
                20                  25                  30

Trp Met Thr Trp Val Arg Gln Pro Pro Gly Lys Gly Leu Glu Trp Val
            35                  40                  45

Gly Arg Ile Lys Ser Thr Thr Asp Gly Thr Thr Asn Tyr Ala Ala
        50                  55                  60

Pro Val Glu Gly Arg Phe Thr Ile Ser Arg Asp Asp Ser Lys Asn Thr
 65                  70                  75                  80

Leu Tyr Leu Glu Met Asn Ser Leu Arg Ala Glu Asp Thr Ala Val Tyr
                85                  90                  95

Tyr Cys Ala Arg Ile Pro Leu Phe Asn His Asp Ser Gly Gly Tyr His
            100                 105                 110

Gly Ala Phe Asp Ile Trp Gly Gln Gly Thr Met Val Thr Val Ser Ser
        115                 120                 125

<210> SEQ ID NO 10
<211> LENGTH: 5
<212> TYPE: PRT
<213> ORGANISM: Artificial Sequence
<220> FEATURE:
<223> OTHER INFORMATION: CDR1 of a heavy chain variable region
```

```
<400> SEQUENCE: 10

Asp Ala Trp Met Thr
 1               5

<210> SEQ ID NO 11
<211> LENGTH: 19
<212> TYPE: PRT
<213> ORGANISM: Artificial Sequence
<220> FEATURE:
<223> OTHER INFORMATION: CDR2 of a heavy chain variable region

<400> SEQUENCE: 11

Arg Ile Lys Ser Thr Thr Asp Gly Gly Thr Thr Asn Tyr Ala Ala Pro
 1               5                  10                  15

Val Glu Gly

<210> SEQ ID NO 12
<211> LENGTH: 17
<212> TYPE: PRT
<213> ORGANISM: Artificial Sequence
<220> FEATURE:
<223> OTHER INFORMATION: CDR3 of a heavy chain variable region

<400> SEQUENCE: 12

Ile Pro Leu Phe Asn His Asp Ser Gly Gly Tyr His Gly Ala Phe Asp
 1               5                  10                  15

Ile

<210> SEQ ID NO 13
<211> LENGTH: 110
<212> TYPE: PRT
<213> ORGANISM: Artificial Sequence
<220> FEATURE:
<223> OTHER INFORMATION: a light chain variable region

<400> SEQUENCE: 13

Gln Leu Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Phe Val Ser Trp Tyr Gln His Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Ala Gly Leu Gln
 65                  70                  75                  80

Thr Gly Asp Asp Ala Asp Tyr Tyr Cys Gly Thr Trp Asp Ser Ser Leu
                85                  90                  95

Ser Ala Tyr Val Phe Gly Thr Gly Ala Lys Val Thr Val Leu
            100                 105                 110

<210> SEQ ID NO 14
<211> LENGTH: 13
<212> TYPE: PRT
<213> ORGANISM: Artificial Sequence
<220> FEATURE:
<223> OTHER INFORMATION: CDR1 of a light chain variable region

<400> SEQUENCE: 14

Ser Gly Ser Ser Ser Asn Ile Gly Asn Asn Phe Val Ser
 1               5                  10
```

```
<210> SEQ ID NO 15
<211> LENGTH: 7
<212> TYPE: PRT
<213> ORGANISM: Artificial Sequence
<220> FEATURE:
<223> OTHER INFORMATION: CDR2 of a light chain variable region

<400> SEQUENCE: 15

Asp Asn Asn Lys Arg Pro Ser
 1               5

<210> SEQ ID NO 16
<211> LENGTH: 11
<212> TYPE: PRT
<213> ORGANISM: Artificial Sequence
<220> FEATURE:
<223> OTHER INFORMATION: CDR3 of a light chain variable region

<400> SEQUENCE: 16

Gly Thr Trp Asp Ser Ser Leu Ser Ala Tyr Val
 1               5                  10

<210> SEQ ID NO 17
<211> LENGTH: 108
<212> TYPE: PRT
<213> ORGANISM: Artificial Sequence
<220> FEATURE:
<223> OTHER INFORMATION: a light chain variable region

<400> SEQUENCE: 17

Gln Leu Val Leu Thr Gln Ser Pro Ser Val Ser Val Ala Pro Gly Gln
 1               5                  10                  15

Thr Ala Arg Ile Thr Cys Gly Gly Asp Asn Ile Gly Arg Glu Ser Val
             20                  25                  30

His Trp Tyr Gln Gln Lys Ala Gly Gln Ala Pro Val Leu Val Ile Tyr
         35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Trp Val Asp Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
            100                 105

<210> SEQ ID NO 18
<211> LENGTH: 11
<212> TYPE: PRT
<213> ORGANISM: Artificial Sequence
<220> FEATURE:
<223> OTHER INFORMATION: CDR1 of a light chain variable region

<400> SEQUENCE: 18

Gly Gly Asp Asn Ile Gly Arg Glu Ser Val His
 1               5                  10

<210> SEQ ID NO 19
<211> LENGTH: 7
<212> TYPE: PRT
<213> ORGANISM: Artificial Sequence
<220> FEATURE:
<223> OTHER INFORMATION: CDR2 of a light chain variable region

<400> SEQUENCE: 19

Tyr Asp Ser Asp Arg Pro Ser
```

```
  1               5

<210> SEQ ID NO 20
<211> LENGTH: 11
<212> TYPE: PRT
<213> ORGANISM: Artificial Sequence
<220> FEATURE:
<223> OTHER INFORMATION: CDR3 of a light chain variable region

<400> SEQUENCE: 20

Gln Val Trp Asp Ser Ser Ser Asp His Val Val
  1               5                  10

<210> SEQ ID NO 21
<211> LENGTH: 114
<212> TYPE: PRT
<213> ORGANISM: Artificial Sequence
<220> FEATURE:
<223> OTHER INFORMATION: a light chain variable region

<400> SEQUENCE: 21

Asp Ile Gln Met Thr Gln Ser Pro Ser Ser Leu Ala Val Ser Leu Gly
  1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Pro Glu Asp Phe Ala Ser Tyr Tyr Cys Gln Glu
                 85                  90                  95

Ser Tyr Ser Ala Pro Tyr Thr Phe Gly Gln Gly Thr Lys Val Glu Ile
            100                 105                 110

Lys Arg

<210> SEQ ID NO 22
<211> LENGTH: 17
<212> TYPE: PRT
<213> ORGANISM: Artificial Sequence
<220> FEATURE:
<223> OTHER INFORMATION: CDR1 of a light chain variable region

<400> SEQUENCE: 22

Lys Ser Ser Gln Ser Val Leu Tyr Ser Asn Asn Lys Asn Tyr Leu
  1               5                  10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: CDR2 of a light chain variable region

<400> SEQUENCE: 23

Trp Ala Ser Thr Arg Glu Ser
  1               5

<210> SEQ ID NO 24
<211> LENGTH: 9
<212> TYPE: PRT
```

```
<213> ORGANISM: Artificial Sequence
<220> FEATURE:
<223> OTHER INFORMATION: CDR3 of a light chain variable region

<400> SEQUENCE: 24

Gln Glu Ser Tyr Ser Ala Pro Tyr Thr
  1               5

<210> SEQ ID NO 25
<211> LENGTH: 38
<212> TYPE: DNA
<213> ORGANISM: Artificial Sequence
<220> FEATURE:
<223> OTHER INFORMATION: Forward primer for D1-D2 domain of VCAM-1

<400> SEQUENCE: 25 caggggccg tggggccctt taaaatcgag accacccc                              38

<210> SEQ ID NO 26
<211> LENGTH: 40
<212> TYPE: DNA
<213> ORGANISM: Artificial Sequence
<220> FEATURE:
<223> OTHER INFORMATION: Reverse primer for D1-D2 domain of VCAM-1

<400> SEQUENCE: 26
tagcggccga cgcggccaat tgcaattctt ttacagcctg                           40

<210> SEQ ID NO 27
<211> LENGTH: 38
<212> TYPE: DNA
<213> ORGANISM: Artificial Sequence
<220> FEATURE:
<223> OTHER INFORMATION: Forward primer for D1-D4 domain of VCAM-1

<400> SEQUENCE: 27 caggggccg tggggccctt taaaatcgag accacccc                              38

<210> SEQ ID NO 28
<211> LENGTH: 39
<212> TYPE: DNA
<213> ORGANISM: Artificial Sequence
<220> FEATURE:
<223> OTHER INFORMATION: Reverse primer for D1-D4 domain of VCAM-1

<400> SEQUENCE: 28
tagcggccga cgcggccaag agctccacct ggattccct                            39

<210> SEQ ID NO 29
<211> LENGTH: 50
<212> TYPE: DNA
<213> ORGANISM: Artificial Sequence
<220> FEATURE:
<223> OTHER INFORMATION: Forward primer for heavy chain

<400> SEQUENCE: 29
ttggtggcca cagcggccga tgtccactcg cagatgcagc tggtgcagtc                50

<210> SEQ ID NO 30
<211> LENGTH: 26
<212> TYPE: DNA
<213> ORGANISM: Artificial Sequence
<220> FEATURE:
<223> OTHER INFORMATION: Reverse primer for heavy chain

<400> SEQUENCE: 30
gaggaggcta gctgaggaga cggtga                                          26
```

<210> SEQ ID NO 31
<211> LENGTH: 50
<212> TYPE: DNA
<213> ORGANISM: Artificial Sequence
<220> FEATURE:
<223> OTHER INFORMATION: Forward primer for heavy chain

<400> SEQUENCE: 31
ttggtggcca cagcggccga tgtccactcg caggtgcagc tggtggagtc          50

<210> SEQ ID NO 32
<211> LENGTH: 50
<212> TYPE: DNA
<213> ORGANISM: Artificial Sequence
<220> FEATURE:
<223> OTHER INFORMATION: Forward primer for light chain of 4B

<400> SEQUENCE: 32
ttggtggcca cagcggccga tgtccactcg cagcctgtgc tgactcagcc          50

<210> SEQ ID NO 33
<211> LENGTH: 34
<212> TYPE: DNA
<213> ORGANISM: Artificial Sequence
<220> FEATURE:
<223> OTHER INFORMATION: Reverse primer for light chain of 4B

<400> SEQUENCE: 33
gaggagagat ctttaggacg gtgaccttgg tccc          34

<210> SEQ ID NO 34
<211> LENGTH: 50
<212> TYPE: DNA
<213> ORGANISM: Artificial Sequence
<220> FEATURE:
<223> OTHER INFORMATION: Forward primer for light chain of 7C

<400> SEQUENCE: 34
ttggtggcca cagcggccga tgtccactcg cagcctgtgc tgactcaatc          50

<210> SEQ ID NO 35
<211> LENGTH: 34
<212> TYPE: DNA
<213> ORGANISM: Artificial Sequence
<220> FEATURE:
<223> OTHER INFORMATION: Reverse primer for light chain of 7C

<400> SEQUENCE: 35
gaggagagat ctttaggacg gtcagcttgg tccc          34

<210> SEQ ID NO 36
<211> LENGTH: 53
<212> TYPE: DNA
<213> ORGANISM: Artificial Sequence
<220> FEATURE:
<223> OTHER INFORMATION: Forward primer for light chain of 7H

<400> SEQUENCE: 36
ttggtggcca cagcggccga tgtccactcg gacatccaga tgacccagtc tcc          53

<210> SEQ ID NO 37
<211> LENGTH: 30
<212> TYPE: DNA
<213> ORGANISM: Artificial Sequence
<220> FEATURE:
<223> OTHER INFORMATION: Reverse primer for light chain of 7H

```
<400> SEQUENCE: 37
gaggagagat cttttgatct ccactttggt                                    30

<210> SEQ ID NO 38
<211> LENGTH: 18
<212> TYPE: DNA
<213> ORGANISM: Artificial Sequence
<220> FEATURE:
<223> OTHER INFORMATION: Primer for CMV-proF

<400> SEQUENCE: 38
aaatgggcgg taggcgtg                                                 18
```

HUMAN MONOCLONAL ANTIBODY THAT SPECIFICALLY BINDS TO VCAM-1 AND A COMPOSITION FOR TREATING AN INFLAMMATORY DISEASE OR A CANCER COMPRISING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_001_01US_ST25.txt. The text file is 15 KB, was created on Mar. 30, 2012, and is being submitted electronically via EFS-Web.

CROSS-REFERENCE TO RELATED APPLICATIONS

This application is a U.S. national stage application filed under 35 U.S.C. §371 of International Patent Application No. PCT/KR2010/001988, accorded an international filing date of Mar. 31, 2010, which claims priority to Korean Patent Application No. 10-2009-0027721, filed Mar. 31, 2009.

TECHNICAL FIELD

The present invention relates to a human monoclonal antibody that specifically binds to VCAM-1, and a therapeutic composition for inflammatory disease or cancer comprising the same. More particularly, the present invention relates to a human monoclonal antibody that specifically binds to VCAM-1, which shows a strong specificity and affinity to human vascular cell adhesion molecule-1 (VCAM-1), and effectively inhibits the interaction between leukocytes and activated endothelial cells expressing VCAM-1, and shows low immunogenicity, and to a therapeutic composition for inflammatory disease or cancer comprising the same.

BACKGROUND ART

During migration from the blood stream to tissue, immune cells including leukocytes pass through activated endothelial cells to induce immune responses, and many cell adhesion molecules (CAMs), such as integrins, selectins, ICAMs (intracellular adhesion molecule) and VCAMs (vascular cell adhesion molecule), are involved in the adhesion of leukocytes to endothelial cells and their migration to the tissue. Cell adhesion molecules are functionally divided into selectins involved in interaction between leukocytes and endothelial cells, integrins involved in adhesion of leukocytes to endothelial cells, immunoglobulins or the like. These cell adhesion molecules play important roles in many physiological responses such as immune responses, inflammation, and thrombosis.

VCAM-1 is a vascular endothelial cell adhesion molecule, which interacts with integrin (VLA-4) expressed on the surfaces of most leukocytes, excluding neutrophils. VCAM-1 is highly induced on activated endothelial cells by inflammatory signals, and is involved in attachment of leukocytes to the vascular endothelial cells and the subsequent transendothelial migration of leukocytes into the damaged tissues.

Despite lots of publications regarding with the role of VCAM-1 in inflammation and cancer and VLA-4 interaction, the development of a neutralizing antibody to VCAM-1 has not been actively studied. Although M/K-2.7, a monoclonal antibody to mouse VCAM-1, was recently developed and shows an inhibitory effect on joint inflammation in a collagen-induced arthritis mouse model, the antibody is specific only to a mouse model and thus the usefulness of the antibody should be further tested for clinical application.

Further, VCAM-1 consists of seven IgG-like domains and its domains 1 and 4 are substantially involved in binding with the ligand, integrin ($\alpha 4\beta 1$ or $\alpha 4\beta 7$) (1995, PNAS, 92:p 5714; 1995, The journal of immunology, 155: p 3135 et al.). Therefore, in order to inhibit the interaction between a VCAM-1 antigen and its ligand, effective neutralizing antibodies should have a strong affinity to domain 1 or 4. In this regard, there is an urgent need to develop a fully human monoclonal antibody which shows a specific cross-reactivity between mouse and human VCAM-1 for preclinical and clinical study, which effectively inhibits the interaction between VCAM-1 antigen and integrin, and minimizes the risk of immunogenicity.

DISCLOSURE

Technical Problem

Accordingly, the present inventors have made many efforts to develop a human monoclonal antibody which shows a specific cross-reactivity to mouse and human VCAM-1, effectively inhibits the interaction between VCAM-1 antigen and integrin, and minimizes the risk of immunogenicity. The inventors have prepared a novel human monoclonal antibody specific to human and mouse VCAM-1 which contains human originated heavy chain and light chain domains from human antibody library, and they have found that the antibody binds to the domain 1-2 or 3-4 of VCAM-1 antigen to exhibit a strong activity of inhibiting the interaction between U397 promonocytic leukocytes and activated endothelial cells, thereby completing the present invention.

Technical Solution

It is an object of the present invention to provide a human monoclonal antibody that specifically binds to human vascular cell adhesion molecule-1 (VCAM-1) to inhibit the interaction of leukocytes with activated endothelial cells, comprising human originated heavy chain ($V_H$) and light chain ($V_L$) domains.

It is another object of the present invention to provide a composition for diagnosing inflammatory disease or cancer, comprising the human monoclonal antibody that specifically binds to VCAM-1.

It is still another object of the present invention to provide a method of providing information for the diagnosis of inflammatory disease or cancer, comprising the step of detecting antigen-antibody reaction between VCAM-1 in a biological sample of a subject suspected of having inflammatory disease or cancer and the human monoclonal antibody that specifically binds to VCAM-1.

It is still another object of the present invention to provide a therapeutic composition for inflammatory disease or cancer using the human monoclonal antibody that inhibits VCAM-1 mediated leukocyte adhesion to endothelial cells.

It is still another object of the present invention to provide a method for treating inflammatory disease or cancer by administration of the therapeutic composition according to the present invention into a subject.

It is still another object of the present invention to provide a method of inhibiting VCAM-1 mediated leukocyte adhesion to endothelial cells using the monoclonal antibody according to the present invention.

Advantageous Effects

The human monoclonal antibody according to the present invention shows a strong affinity to VCAM-1 expressed on human or mouse endothelial cells, effectively inhibits leukocyte adhesion to activated endothelial cells expressing VCAM-1, and has human-derived heavy chain and light chain domains to show a low immunogenicity, thereby being used for the treatment of cancer or inflammatory disease such as asthma, rhinitis, arthritis, multiple sclerosis, bowel disease, arteriosclerosis, myocardial infarction and transplant rejection.

DESCRIPTION OF DRAWINGS

FIG. 2 shows the amino acid sequences (SEC) ID Nos. 1-24) of variable regions of three types of human monoclonal antibodies according to the present invention;

FIG. 3 is the result of ELISA (Enzyme-linked immunosorbent assay) showing the affinity of antigen-specific anti VCAM-1 human monoclonal antibodies to antigens according to their human VCAM-1 domains, in which VD2 represents a recombinant human VCAM-1 domain D1-D2/Fc chimera, VD4 represents a recombinant human VCAM-1 domain D1-D4/Fc chimera, and VD7 represents recombinant human VCAM-1 domain D1-D7/Fc chimera;

BEST MODE

Figure 1:
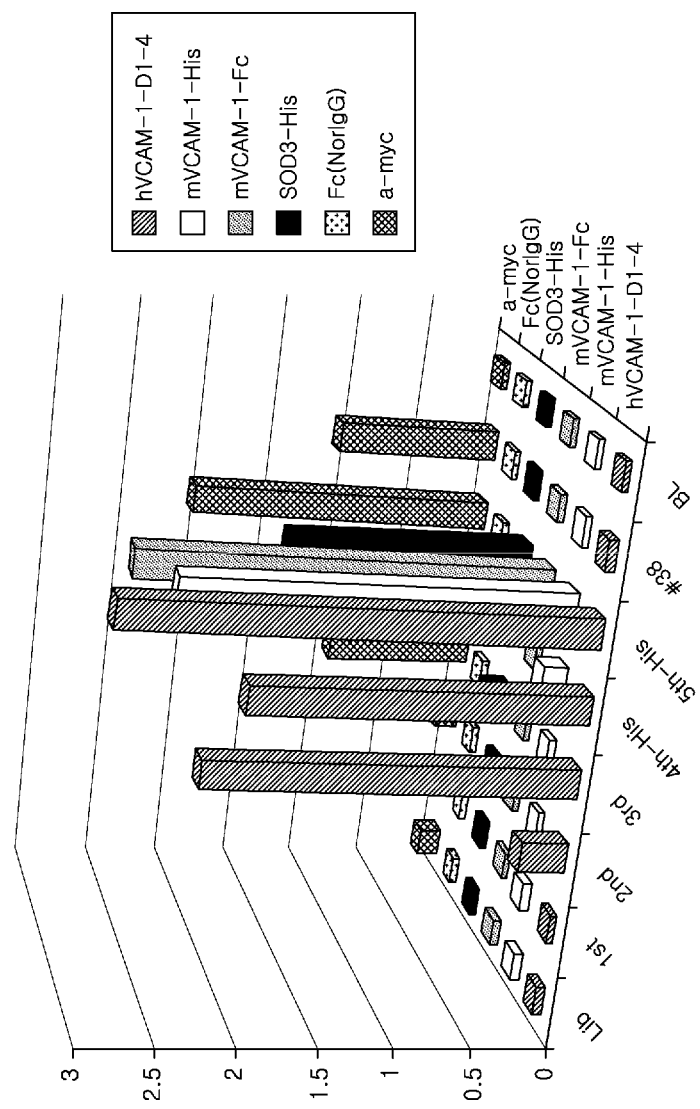
FIG. 1 shows the result of panning performed using human VCAM-1-D1-D4 and mouse VCAM-1 antigen.

To achieve the above objects, one aspect of the present invention is to provide a human monoclonal antibody that specifically binds to human vascular cell adhesion molecule-1 (VCAM-1) to inhibit the interaction between leukocytes and activated endothelial cells.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies).

The term "antibody" also includes antigen binding forms of antibodies, including fragments with antigen-binding capability (e.g., Fab', F(ab')2, Fab, Fv and rIgG). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992, J. Immunol. 148:15467), Pack and Pluckthun (1992, Biochemistry 31:1579), Hollinger et al. (1993, supra), Gruber et al. (1994, J. Immunol.: 5368), Zhu et al. (1997, Protein Sci. 6:781), Hu et al. (1996, Cancer Res. 56:3055), Adams et al. (1993, Cancer Res. 53:4026) and McCartney et al. (1995, Protein Eng. 8:301).

Also, the term "monoclonal antibody" as used herein, refers to an antibody molecule that has been obtained from a substantially identical antibody clone, which shows single-binding specificity and affinity for a specific epitope.

Typically, an immunoglobulin has a heavy and light chain. Each heavy and light chain contains a constant region and a variable region (the regions are also known as "domains"). Light chain and heavy chain variable regions contain three hypervariable regions called "complementarity-determining regions" or "CDRs" and four "framework" regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

As used herein, the term "humanized antibody" is a molecule derived from human immunoglobulin, and means that all amino acid sequences constituting an antibody, including complementarity-determining regions and framework regions, are composed of human immunoglobulin. Humanized antibodies generally have at least three potential advantages for use in human therapy. First, it may interact better with the human immune system, e.g., to destroy target cells more efficiently by complement-dependent cytotoxicity (CDC) or antibody-dependent cellular cytotoxicity (ADCC). Second, the human immune system does not recognize the antibody as foreign. Third, the half-life in the human circulation will be similar to that of naturally occurring human antibodies, allowing smaller and less frequent doses to be given. Therefore, the human monoclonal antibodies according to the present invention show a strong affinity to VCAM-1 expressed on human endothelial cells, and effectively inhibit leukocyte adhesion to activated endothelial cells expressing VCAM-1. In addition, since their heavy chain and light chain domains are all derived from human to show low immunogenicity, the human monoclonal antibodies according to the present invention can be used for the treatment of cancer or inflammatory disease such as asthma, rhinitis, arthritis, multiple sclerosis, bowel disease, arteriosclerosis, myocardial infarction and transplant rejection.

As used herein, the term "inhibition of the interaction between leukocytes and activated endothelial cells" means all mechanisms such that the human monoclonal antibody of the present invention specifically binds to VCAM-1 expressed on an activated endothelial cell to inhibit the interaction between VLA-4 (very late antigen-4) and α4β1 integrin expressed on leukocytes and VCAM-1 expressed on endothelial cells, or inhibits the gap formation between endothelial cells. The interaction inhibition is not limited thereto, but for example, can be performed by inhibition of leukocyte adhesion to activated endothelial cells or inhibition of gap formation between endothelial cells by reduction of ROS (Reactive oxygen species) and RhoA (Ras homolog gene family, member A) activity. When immune cells such as leukocytes bind to endothelial cells, the intracellular RhoA and ROS in the endothelial cell signaling pathway are activated to trigger the signal transduction for loosening of the firm connection of molecules which link cells. Subsequently, the gap between endothelial cells is enlarged to form a hole. Immune cells pass through the hole, and migrate into the inflamed site. However, the antibody of the present invention reduces the ROS and RhoA activity in the endothelial cell signaling pathway, so that the gap formation between endothelial cells is inhibited not to form a hole. Consequently, migration of immune cells into an inflamed site is prevented, thereby inhibiting the interaction between leukocytes and activated endothelial cells.

Figure 4:
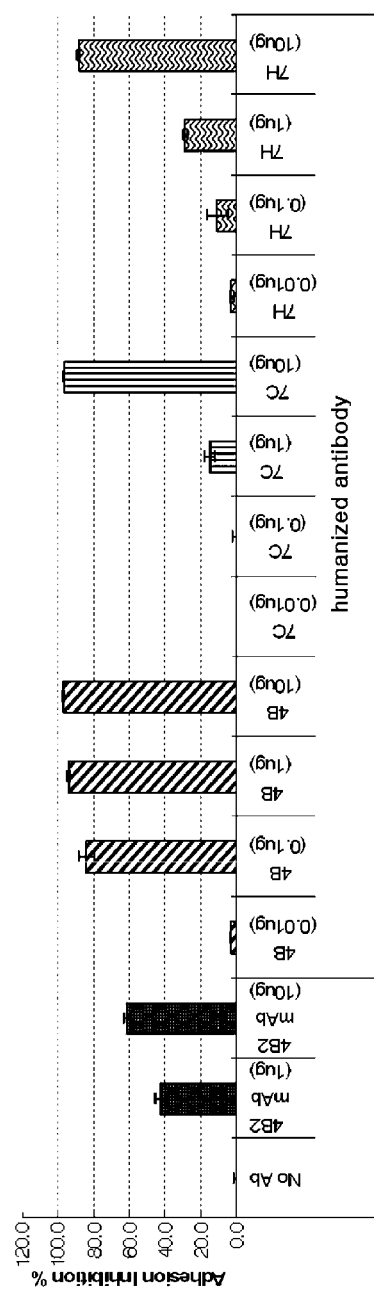
FIG. 4 is the result of analyzing the inhibitory activity of anti VCAM-1 human monoclonal antibodies on the adhesion between purified human recombinant VCAM-1 antigens and human leukocytes, in which their inhibitory activity is determined by reduction in fluorescence intensity, compared to that of a non-antibody-treated group.
Figure 5:
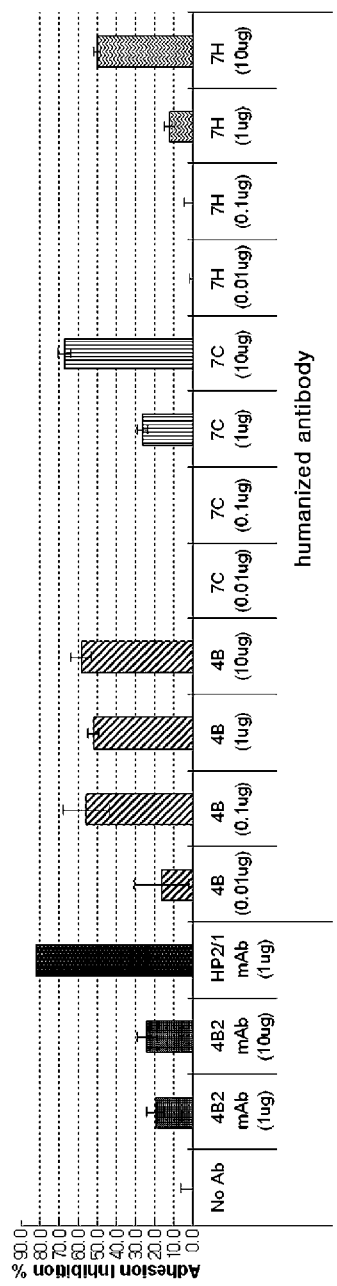
FIG. 5 is the result of analyzing the inhibitory activity of anti VCAM-1 human monoclonal antibodies on the adhesion between human leukocytes and human endothelial cells activated with TNF-α(Tumor necrosis factor-α), in which their inhibitory activity is determined by reduction in fluorescence intensity, compared to that of a non-antibody-treated group.

In accordance with one embodiment of the present invention, it was found that the human monoclonal antibody 4B of the present invention showed an 80% inhibition rate on leukocyte adhesion to human VCAM-1 antigen at an amount of 0.1 μg or more, and the human monoclonal antibodies 7C and 7H of the present invention showed a 90% or more inhibition rate on leukocyte adhesion to human VCAM-1 antigen at an amount of 10 μg (FIG. 4). Further, it was found that the human monoclonal antibody 4B of the present invention showed a 50~60% inhibition rate on leukocyte adhesion to human endothelial cell at an amount of 0.1-10.0 μg, and the human monoclonal antibodies 7C and 7H of the present invention showed a 50~60% or more inhibition rate on leukocyte adhesion to human endothelial cell at an amount of 10 μg (FIG. 5). The results indicate that the antibodies of the present invention effectively inhibit the leukocyte adhesion to activated endothelial cells. In addition, it was found that the human monoclonal antibody 4B showed about 80% RhoA inhibition, and the human monoclonal antibody 7H showed about 30% RhoA inhibition (FIG. 6), and the human monoclonal antibody 4B showed about 65% ROS inhibition, and the human monoclonal antibody 7H showed about 25% ROS inhibition (FIG. 7), indicating that the antibodies of the present invention effectively reduce RhoA and ROS activity to prevent gap formation between endothelial cells. These results suggest that the inhibitory effects of these antibodies on the interaction between leukocyte and activated endothelial cells will be useful for diagnosis and treatment of VCAM-1-related disease such as inflammatory disease or cancer.

In a preferred embodiment, the human monoclonal antibody of the present invention may include a heavy chain variable region that contains a heavy chain CDR1 as defined by SEQ ID NO. 2; a heavy chain CDR2 as defined by SEQ ID NO. 3; and a heavy chain CDR3 as defined by SEQ ID NO. 4, and a light chain variable region that contains a light chain CDR1 as defined by SEQ ID NO. 14; a light chain CDR2 as defined by SEQ ID NO. 15; and a light chain CDR3 as defined by SEQ ID NO. 16. More preferably, the human monoclonal antibody of the present invention may include a heavy chain amino acid sequence as defined by SEQ ID NO. 1 and a light chain amino acid sequence as defined by SEQ ID NO. 13. In accordance with one embodiment of the present invention, the human monoclonal antibody including a heavy chain amino acid sequence as defined by SEQ ID NO. 1 and a light chain amino acid sequence as defined by SEQ ID NO. 13 is designated as 4B.

In accordance with one preferred embodiment, the human monoclonal antibody provides an affinity to human VCAM-1, and an association/dissociation constant ($K_D$ value) of human monoclonal antibody to human VCAM-1 antigen may be $1\times10^{-11}$ M to $9\times10^{-9}$ M, which can be obtained by determining the association/dissociation constant ($K_D$ value) of each antibody to human VCAM-1 antigen using a BIACORE analysis. In accordance with one embodiment of the present invention, the human monoclonal antibody 4B was found to have a strong affinity of about 1 nM to human VCAM-1 antigen (Table 1), suggesting that the antibody of the present invention has a strong specific affinity to VCAM-1, and therefore, the antibody of the present invention can be used in any application that requires antigen recognition to VCAM-1.

In accordance with one preferred embodiment, the human monoclonal antibody of the present invention may be a human monoclonal antibody that specifically binds to mouse vascular cell adhesion molecule-1 (VCAM-1), as well as human VCAM-1, so as to inhibit the interaction between leukocytes and activated endothelial cells. Such a monoclonal antibody is advantageous in that it binds to both human and mouse VCAM-1, namely, has cross-reactivity, thereby being useful for preclinical study in mice.

The human monoclonal antibody that specifically binds to both human and mouse vascular cell adhesion molecule-1 (VCAM-1) may include a heavy chain variable region that contains a heavy chain CDR1 as defined by SEQ ID NO. 6; a heavy chain CDR2 as defined by SEQ ID NO. 7; and a heavy chain CDR3 as defined by SEQ ID NO. 8, and a light chain variable region that contains a light chain CDR1 as defined by SEQ ID NO. 18; a light chain CDR2 as defined by SEQ ID NO. 19; and a light chain CDR3 as defined by SEQ ID NO. 20. More preferably, the human monoclonal antibody of the present invention may include a heavy chain amino acid sequence as defined by SEQ ID NO. 5 and a light chain amino acid sequence as defined by SEQ ID NO. 17. In accordance with one embodiment of the present invention, the human monoclonal antibody including a heavy chain amino acid sequence as defined by SEQ ID NO. 5 and a light chain amino acid sequence as defined by SEQ ID NO. 17 is designated as 7C.

Further, the human monoclonal antibody that specifically binds to both human and mouse vascular cell adhesion molecule-1 (VCAM-1) may include a heavy chain variable region that contains a heavy chain CDR1 as defined by SEQ ID NO. 10; a heavy chain CDR2 as defined by SEQ ID NO. 11; and a heavy chain CDR3 as defined by SEQ ID NO. 12, and a light chain variable region that contains a light chain CDR1 as defined by SEQ ID NO. 22; a light chain CDR2 as defined by SEQ ID NO. 23; and a light chain CDR3 as defined by SEQ ID NO. 24. More preferably, the human monoclonal antibody of the present invention may include a heavy chain amino acid sequence as defined by SEQ ID NO. 9 and a light chain amino acid sequence as defined by SEQ ID NO. 21. In accordance with one embodiment of the present invention, the human monoclonal antibody including a heavy chain amino acid sequence as defined by SEQ ID NO. 9 and a light chain amino acid sequence as defined by SEQ ID NO. 21 is designated as 7H.

In accordance with one preferred embodiment, the human monoclonal antibody provides an affinity to human VCAM-1, and the association/dissociation constant ($K_D$ value) of human monoclonal antibody to human and mouse VCAM-1 antigen may be $1\times10^{-10}$ M to $9\times10^{-8}$ M, which can be obtained by determining the association/dissociation constant ($K_D$ value) of each antibody to human VCAM-1 using a BIACORE analysis. In accordance with one embodiment of the present invention, the human monoclonal antibodies 7C and 7H were found to have a high affinity of about 5~100 nM to human and mouse VCAM-1 antigen (Table 1), suggesting that the antibody of the present invention has a strong specific affinity to human and mouse VCAM-1, and therefore, the antibody of the present invention can be used in any application that requires antigen recognition to VCAM-1. That is, the human monoclonal antibody of the present invention has a strong specific affinity to human VCAM-1, or human and mouse VCAM-1 to effectively inhibit leukocyte adhesion to activated endothelial cells, thereby providing an effective diagnosis and treatment method for VCAM-1-related diseases such as inflammatory disorder or cancer.

In still another aspect, the present invention relates to a method for preparing a human monoclonal antibody that specifically binds to human, or human and mouse VCAM-1.

The monoclonal antibody of the present invention can easily be produced by well-known methods for producing a monoclonal antibody. For example, the method for preparing a monoclonal antibody may be performed by producing a hybridoma using B leukocytes obtained from immunized animals (Kohler and Milstein, 1975, Nature, 256:495), or using phage display method, but is not limited thereto.

An antibody library using phage display is a method of expressing an antibody on the surface of a phage with genes of the antibody directly obtained from B lymphocytes without preparation of hybridoma. Many of the difficulties associated with generating monoclonal antibodies by B-cell immortalization can be overcome by the phage display method. A conventional phage display comprises: 1) inserting an oligonucleotide having a random sequence into the region corresponding to the N-terminus of a phage coat protein pIII (or pIV); 2) expressing a fusion protein of a natural coat protein and a polypeptide coded by said oligonucleotide having a random sequence; 3) treating a receptor material that can bind to the polypeptide coded by said oligonucleotide; 4) eluting peptide-phage particles bound to the receptors using low pH or a molecule which has binding competitiveness; 5) amplifying the eluted phage in a host cell by panning; 6) repeating said steps for obtaining desired amounts of phage; and 7) determining a sequence of an active peptide with the DNA sequencing of phage clones selected by panning.

In a preferred embodiment, a preparation method of the monoclonal antibody of the present invention may be performed by phage display method. A person skilled in the art to which the present invention pertains can perform the above steps easily referring to well-known phage display techniques, which are disclosed in, for example, Barbas et al. (METHODS: A Companion to Methods in Enzymology 2: 119, 1991 and J. Virol. 2001 July; 75(14):6692-9) and Winter et al. (Ann. Rev. Immunol. 12:433, 1994). A phage which can be used for constructing the antibody library may be a filamentous phage, for example, fd, M13, f1, If1, Ike, Zj/Z, Ff, Xf, Pf1 or Pf3, but is not limited thereto. Also, a vector, which can be used for the expression of a heterogeneous gene on the surface of the filamentous phage, may be a phage vector such as fUSE5, fAFF1, fd-CAT1 or fdtetDOG, or a phagemid vector such as pHEN1, pComb3, pComb8 or pSEX, but is not limited thereto.

Further, a helper phage, which can be used for providing a natural coat protein required for successful re-infection of recombinant phage, may be exemplified by M13K07 or VSCM13, but is not limited thereto.

In accordance with one embodiment of the present invention, the molecular weight and purity of VCAM-1 obtained by recombination technique were examined, and then used for the preparation of monoclonal antibody. A human antibody specific to human and mouse VCAM-1 was obtained as human-derived scFv (single-chain variable fragment) by phage display technology, and screened as a mono phage clone, thereby obtaining 22 types of monoclone phages being specific to both human, or human and mouse VCAM-1. The monoclone phages were obtained as follows. First, VCAM-1 was reacted with a library phage from human naive scFv library cells having diversity, followed by panning and screening of mono clones strongly binding to VCAM-1 antigen (Table 1 and FIG. 2). The selected mono clones were confirmed by fingerprinting, followed by sequencing to confirm CDR regions of VH and VL of the antibody. The Homology between the above antibody and germ line antibody group was investigated by the Ig BLAST program of the NCBI web-site (ncbi.nlm.nih.gov/igblast/). As a result, 22 types of phage antibodies being specific to VCAM-1 were obtained.

Further, in accordance with one embodiment of the present invention, an expression vector containing a polynucleotide encoding the heavy chain and light chain of the selected 22 types of human antibody phage or the fragment thereof having immunological activity was constructed. Upon construction of the expression vector, expression regulatory elements, such as a promoter, a terminator, and an enhancer, and a sequence for targeting membranes or secretion can be properly selected and used in combination for a purpose, depending on a host cell intended to produce the light chain and heavy chain of the human antibody or the fragment thereof.

The expression vector of the present invention includes a plasmid vector, a cosmid vector, a bacteriophage vector, a viral vector or the like, but is not limited thereto. A suitable expression vector includes a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof.

Figure 3:
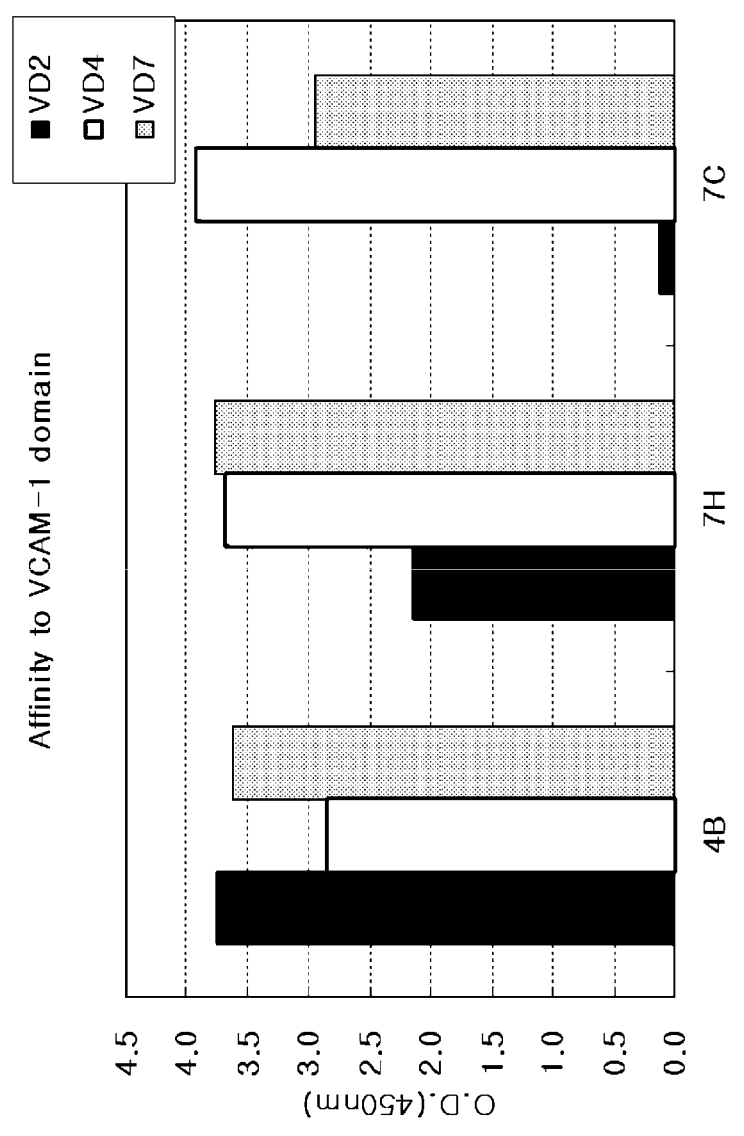

Further, according to one embodiment of the present invention, the present invention provides a method of identifying the location of the domains of human VCAM-1 antigen, which bind with a human antibody. It has been reported that VCAM-1 consists of seven IgG-like domains and its domains 1 and 4 are substantially involved in binding with its ligand, integrin ($\alpha 4\beta 1$ or $\alpha 4\beta 7$). In accordance with one embodiment of the present invention, each domain (D1-D2, D1-D4, D1-D7) of human VCAM-1 antigen was expressed and purified, and then ELISA was performed to analyze antigen-binding regions of 22 types of antibodies. As a result, the antigen-binding regions vary depending on the type of antibodies, and among them, the antibodies 4B and 7H binding to domain D1-D2 and the antibody 7C binding to domain D3-D4 were obtained (FIG. 3).

Further, the interaction between leukocytes and activated endothelial cells is mediated by VCAM-1 in the present invention, thereby analyzing the inhibitory activity of the antibodies on the interaction between human leukocyte (U937 cell) and human endothelial cell (HUVEC) stimulated with recombinant human VCAM-1 or human TNF-$\alpha$. In accordance with one embodiment of the present invention, a human VCAM-1-immobilized solid support plate or a HUVEC monolayer plate is treated with the antibodies at various concentrations. To examine whether the antibodies inhibit binding of the fluorescence-labeled U937 cell and the antigen, fluorescence intensity was measured. As a result, all three types of the antibodies showed inhibitory activity. In particular, the antibody 4B showing the strongest affinity to human VCAM-1 antigen was found to exhibit strong inhibitory activity even at a low concentration (FIGS. 4 and 5).

As the monoclonal antibodies of the present invention have a strong affinity to VCAM-1 expressed in a variety of cell types such as human or mouse, it can be used for any application using antigen-recognition to VCAM-1. Furthermore, the monoclonal antibody potently inhibits the binding of leukocytes to activated endothelial cells. Therefore, the present invention provides an effective method for diagnosing and treating VCAM-1-related diseases such as inflammatory disease, or the like.

Accordingly, the human monoclonal antibody that specifically binds to human, or human and mouse VCAM-1 of the present invention may be used alone or in the form of a pharmaceutical composition for diagnosing and treating VCAM-1-related disease, together with a pharmaceutical acceptable carrier.

Moreover, the monoclonal antibody of the present invention may also be used in combination with other antibodies, bioactive agents or materials for various purposes. For example, the monoclonal antibody of the present invention may be used in combination with 4B9 or other anti-VCAM-1 antibodies in the treatment of disorders characterized by VCAM-1 expression in endothelium. Alternatively, the monoclonal antibody of the present invention may be used in combination with antibodies recognizing other endothelial cell receptors identified in inflammatory events (e.g., ELAM1, ICAM1, etc.) and the known therapeutic drugs for inflammatory disease.

In still another aspect, the present invention provides a composition for diagnosing inflammatory disease or cancer, comprising the human monoclonal antibody.

That is, a diagnostic composition comprising the monoclonal antibody that specifically binds to human, or human and mouse, VCAM-1 is used for the diagnosis of VCAM-1 expression-related diseases or VCAM-1-mediated diseases, for example, inflammatory disease or cancer.

As used herein, the term "inflammatory disease" may include VCAM-1-related inflammatory diseases without limitation, for example, asthma, rhinitis, arthritis, multiple sclerosis, bowel disease, arteriosclerosis, myocardial infarction or transplant rejection.

The composition for diagnosing an inflammatory disease or cancer of the present invention may further include pharmaceutically acceptable carriers, and may be formulated together with the carriers. As used herein, the term "pharmaceutically acceptable carrier" refers to a carrier or diluent that does not cause damage to the biological activity and properties of the active ingredient. For liquid formulation, the pharmaceutically acceptable carriers should be sterilized and suitable to living bodies. For example, the pharmaceutically acceptable carriers may include saline, sterilized water, Ringer's solution, buffered saline, albumin injection solution, dextrose solution, malto dextrin solution, glycerol, ethanol, or the mixture of one or more of the above ingredients. If necessary, other common additives can be added, such as antioxidants, buffers, bacteriostatic agents or the like. Also, diluting agents, dispersing agents, surfactants, binders or lubricants can be further added in order to formulate the composition to injection formulations such as aqueous solution, suspension, and emulsion, pills, capsules, granules, or tablets.

In still another aspect, the present invention provides a method of providing information for the diagnosis of inflammatory disease or cancer, comprising the step of detecting antigen-antibody reaction between VCAM-1 in a biological sample of a subject suspected of having inflammatory disease or cancer and the human monoclonal antibody. That is, VCAM-1 may be detected by reacting the recombinant human monoclonal antibody of the present invention with a biological sample and detecting the formation of an antigen-antibody complex. Consequently, information for the diagnosis of inflammatory disease or cancer may be provided.

As used herein, the term "subject" encompasses horses, dogs, cats, pigs, goats, rabbits, hamsters, monkeys, guinea pigs, rats, mice, lizards, snakes, sheep, cattle, fish and birds without limitation, and means any animal (e.g., human).

As used herein, the term "biological sample" may be a tissue, a cell, whole blood, serum, plasmic fluid, autoptical sample of tissue (brain, skin, lymph node, spinal cord), supernatant of cell culture, disruptive eukaryotic cell and bacterial expression system, but is not limited thereto. Existence of VCAM-1, inflammatory disease or cancer can be detected by reacting a manipulated or non-manipulated biological sample with the monoclonal antibody of the present invention.

As used herein, the term "antigen-antibody complex" refers to a combination material of VCAM-1 antigen in the sample and the monoclonal antibody of the present invention. Formation of such antigen-antibody complex may be detected by a method selected from a group consisting of colormetric method, electrochemical method, fluorimetric method, luminometry, particle counting method, visual assessment and scintillation counting method. However, the method is not limited to the above examples and has a variety of applications.

Various labels may be used for detecting an antigen-antibody complex in the present invention. Specific examples thereof may be selected from the group consisting of enzymes, fluorescent substances, ligands, luminescent substances, microparticles, and radioactive isotopes, but are not limited thereto.

Suitable examples of materials to be used as a label include acetylcholine esterase, alkaline phosphatase, β-D-galactosidase, horseradish peroxidase and β-lactamase as an enzyme; fluorescein, $Eu^{3+}$, $Eu^{3+}$ chelate and cryptate as a fluorescent; biotin-derivatives as a ligand; acridinium ester, isoluminol derivatives as a luminescent; colloidal gold, colored latex as a microparticle; and $^{57}Co$, $^{3}H$, $^{125}I$, $^{125}I$-Bolton Hunter reagent as a radioactive isotopes.

Preferably, the antigen-antibody complex may be detected by using Enzyme-linked immunosorbent assay (ELISA). ELISA techniques include a direct ELISA using a labeled antibody which recognizes an antigen adhered to a support body; an indirect ELISA using a labeled secondary antibody which recognizes a captured antibody of an antigen-antibody complex wherein the antigen adhered to a support body; a direct sandwich ELISA using another labeled antibody which recognizes an antigen of an antigen-antibody complex adhered to a support body; and an indirect sandwich ELISA using another labeled secondary antibody which recognizes an antibody, after reacting with the antibody which recognizes an antigen of an antigen-antibody complex adhered to a support body. The monoclonal antibody may have a detectable label, otherwise the antigen-antibody complex may be detected by treating another antibody which can capture the monoclonal antibody of the present invention and has a detectable label.

In still another embodiment, the present invention provides a therapeutic composition for inflammatory disease or cancer comprising the human monoclonal antibody, and a method for treating inflammatory disease or cancer comprising the step of administering the therapeutic composition into a subject.

The therapeutic composition for inflammatory disease or cancer of the present invention may further include pharmaceutically acceptable carriers, and may be formulated together with the carriers. The useful carriers are the same as the above described.

In this connection, the inflammatory disease may be selected from the group consisting of asthma, rhinitis, arthritis, multiple sclerosis, bowel disease, arteriosclerosis, myocardial infarction and transplant rejection, but is not limited thereto.

Figure 8:
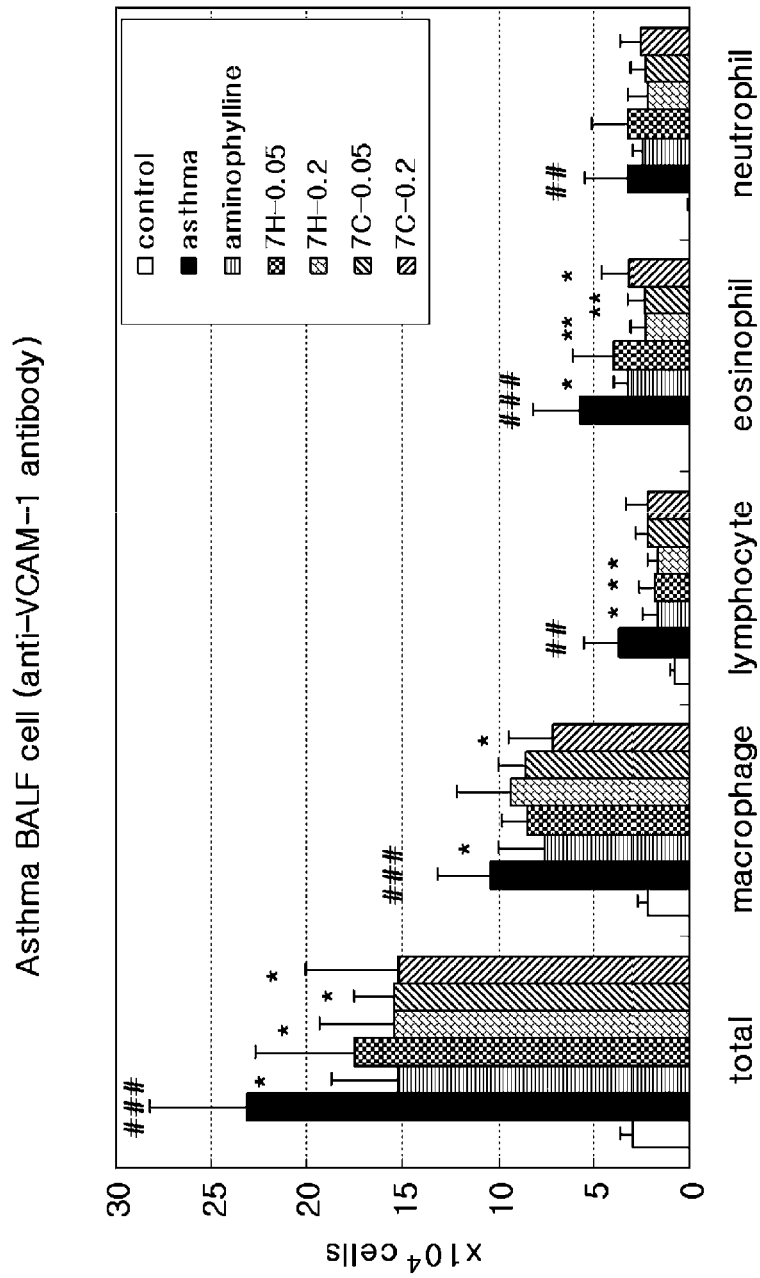
FIG. 8 is the result of analyzing the inhibitory activity of an anti VCAM-1 antibody on infiltration of inflammatory cells into bronchoalveolar lavage fluid in an ovalbumin-induced asthma mouse model (versus the normal group ##, $p<0.01$; ###, $p<0.001$, versus the asthma-induced group *, $p<0.05$; **, $p<0.01$).

In accordance with one embodiment of the present invention, an efficacy test in mouse asthma was performed in order to confirm whether the human monoclonal antibody according to the present invention has an anti-inflammatory effect in vivo. After treatment of anti-VCAM-1 human antibody, the total number of inflammatory cells, in particular, lymphocytes, eosinophils, and macrophages, was significantly reduced. That is, the inhibitory effect of the antibody on inflammatory cell influx in asthma was found to be similar to that of aminophylline which is currently used for the treatment of asthma (FIG. 8).

The therapeutic composition comprising the human monoclonal antibody of the present invention may be administered in single or multiple doses in a pharmaceutically effective amount. In this regard, the composition may be administered in a form of solutions, powders, aerosols, capsules, enteric-coated tablets or capsules or suppositories. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. In addition, the pharmaceutical composition may be administered using a certain apparatus capable of transporting the active ingredients into a target cell.

The composition comprising the monoclonal antibody of the present invention may be administered in a pharmaceutically effective amount. The "pharmaceutically effective amount" refers to an amount sufficient for preventing or treating disease in a reasonable ratio of advantage/risk, which can be applicable to medical treatment or prevention. The level of the effective dosage can be determined according to the severity of the disease; drug activity; the age, weight, health, and sex of a patient; the drug sensitivity in a patient; the administration time, route, and release rate; the treatment duration; or elements including drugs that are blended or simultaneously used with the composition of the present invention, or other elements well-known in the medical field. In addition, the composition comprising the monoclonal antibody of the present invention may be administered singly or in combination with other therapeutic agents, or may be also administered with conventional therapeutic agents in a sequential or simultaneous manner.

In case of administrating the pharmaceutical composition of the present invention in a pharmaceutically effective amount, the monoclonal antibody of the present invention, which has a strong affinity to VCAM-1, specifically binds to VCAM-1 expressed on endothelial cells and results in neutralization of VCAM-1. Ultimately, the monoclonal antibody of the present invention inhibits the adhesion of leukocytes to the endothelial cells, thereby treating VCAM-1-mediated diseases. Preferably, VCAM-1-mediated disease is an inflammatory disease or a cancer, and more preferably, the inflammatory disease is arthritis, rhinitis, multiple sclerosis, bowel disease, asthma, arteriosclerosis, myocardial infarction or transplant rejection.

In still another aspect, the present invention provide a method of inhibiting VCAM-1 mediated leukocyte adhesion to endothelial cells using the human monoclonal antibody according to the present invention. That is, VCAM-1 binds to VLA-4 (very late antigen-4) and a4 µl integrin that are expressed on activated leukocytes in inflammation and immune rejection, and plays a critical role in promoting the interaction between endothelial cells and leukocytes including monocyte and T cells. The monoclonal antibody according to the present invention specifically binds to VCAM-1 to inhibit leukocyte adhesion to endothelial cells.

MODE FOR INVENTION

Hereinafter, the present invention will be described in more detail with reference to the Examples. However, the following Examples are provided only for the purpose of illustrating the present invention, and accordingly it is not intended that the present invention is limited thereto.

Example 1

Preparation of Human and Mouse VCAM-1 Antigen

<1-1>Cloning of Human VCAM-1

A plasmid containing human VCAM-1 gene (hMU012650) (Kugi #IRAU-75-G02) was purchased from KUGI (Korean UniGene Information) provided by the Center for Functional Analysis of Human Genome, Korea Research Institute of Bioscience and Biotechnology (KRIBB). The plasmid was used as a template DNA, and in order to express only the D1-D2 domain and D1-D4 domain of VCAM-1, each gene was amplified using a forward primer (5'-CAGGGGGCCGTGGGGGCCTTTAAAATC-GAGACCACCCC-3', SEQ ID NO. 25) and a reverse primer (5'-TAGCGGCCGACGCGGCCAATTGCAAT-TCTTTTACAGCCTG-3', SEQ ID NO. 26) for the D1-D2 domain of VCAM-1, and a forward primer (5'-CAGGGGGC-CGTGGGGGCCTTTAAAATCGAGACCACCCC-3', SEQ ID NO. 27) and a reverse primer (5'-TAGCGGCCGACGCG-GCCAAGAGCTCCACCTGGATTCCCT-3', SEQ ID NO. 28) for the D1-D4 domain of VCAM-1. After treatment of sfiI, a ligase was used to clone the genes into a pYK602-Fc vector and a pYK602-His only vector (vector constructed by KRIBB), respectively. PCR products were obtained under the following PCR conditions: for a total reaction volume of 50 µl, a template of 100 ng was reacted at 94° C. for 2 min, and then at 94° C. for 30 sec, at 55° C. for 30 sec, and at 72° C. for 1 min 30 sec (D1-D4) and 45 sec (D1-D2) for 30 cycles, and then 10 min at 72° C. Moreover, base sequences of the cloned pYK602-FC-VCAM-1-D1-D2, pYK602-His-VCAM-1-D1-D2, pYK602-FC-VCAM-1-D1-D4, and pYK602-His-VCAM-1-D1-D4 vectors were examined.

<1-2> Expression and Purification of VCAM-1 Protein

In order to select antibodies having cross-reactivity to mVCAM-1 from the antibodies having a strong affinity to hVCAM-1, several proteins were prepared. Among them, the entire molecule-containing hVCAM-Fc-chimera (R&D Systems, cat #: 862-VC) and mVCAM-1-Fc chimera (R&D Systems, Cat #: 643-VM) were commercially purchased, and expression and purification of the fragments with each VCAM-1 domain were performed as follows.

First, $5 \times 10^6$ 293E cells were plated in 10 dishes of 150 mm diameter, and on the next day, each 20 µg of the cloned pYK602-VCAM-1-D1-D2 vector and pYK602-VCAM-1-D1-D4 vector were treated with PEI (23966: Polysciences, Inc, USA) for transfection. The next day, the media was replaced with serum-free DMEM, and then the supernatants were collected every other day, followed by electrophoresis in a 10% SDS-PAGE gel and Western blotting for analysis of expression level.

The supernatants, in which the expression of hVCAM-1-D1-D2-Fc and hVCAM-1-D1-D4-Fc was confirmed, were collected, and filtered using a 0.22 μm top-filter (Millipore, Cat #: SCGP T05 RE) to obtain a sufficient amount of protein. The proteins were purified before use, as follows. First, an ECONO-COLUMN (Bio-Rad Cat. No 737-1006, 1×5 cm) was washed with PBS, and packed with 500 μl of protein A (Amersham Cat. No. 17-1279-30). During the performing of the packing, 10 ml of PBS (pH 7.4) was applied to the column to wash beads, and 30 ml of 20 mM sodium phosphate buffer (pH 7.0) was applied as a binding buffer. Subsequently, the obtained supernatant was applied thereto using a Peri-staltic pump (Bio-Rad Cat. No. 731-8142) at a flow rate of 0.5 ml/min. After binding to the column, it was washed with PBS at a flow rate of 2 ml/min for 1 hr, followed by elution. 500 μl of 0.1 M glycine-HCl (pH 2.5) was used for elution, and 1/10 volume of 1 M Tris-HCl (pH 9.0) was added for neutralization. Among 6 elution fractions, the protein was mainly eluted in #1 and #2 fractions. These two fractions were put in a 10 K dialysis membrane, followed by o/n dialysis in 4 L of PBS. All the above processes were performed in a 4° C. cold room. After quantification, the products were aliquoted and stored at −70° C. After purification, the products were confirmed on 10% SDS-PAGE gel. hVCAM-1-D1-D2-Fc and hVCAM-1-D1-D4-Fc were obtained in an amount of 2.8 mg and 800 μg, respectively. The supernatants, in which the expression of hVCAM-1-D1-D2-his and hVCAM-1-D1-D4-his was confirmed, were collected, filtered using a 0.22 μm top-filter (Millipore, Cat #: SCGP T05 RE) and concentrated using a PELLICON XL membrane (Millipore, 8K, cat #: PXBO 08A 50) of LABSCALE TFF System (Millipore, Cat #: XX42LSS11) to 1/10 volume. 10-fold volume of an IMAC buffer solution (300 mM KCl, 50 mM $KH_2PO_4$, 5 mM imidazole, pH 8.0) was added to the concentrate, and replaced by the IMAC buffer solution. Purification was performed using a BIO-SCALE MINI PROFINITY IMAC cartridge (cat #: 732-4610) of Profinia™ protein Purification System (Bio-Rad) at a rate of 1 ml/min according to the manufacturer's instructions. The eluent was dialyzed using a membrane (10K, 132574:SPECTRAPOR, USA) in 4 L of PBS solution at 4° C. for 4 hr or longer, and then dialyzed again in 4 L of pre-cooled PBS solution overnight. After o/n dialysis, the resultant was transferred to an e-tube, and protein concentration was determined by the Bradford method. Consequently, 400 μg of hVCAM-1-D1-D4-his protein was obtained, and examined in a 10% SDS-PAGE gel.

Example 2

Construction of Library Phage $2.7 \times 10^{10}$ human scFv (single-chain variable fragment) library cells having diversity were cultured in a medium (3 L) containing 17 g of 2×YTCM [Tryptone (CONDA, 1612.00), 10 g of yeast extract (CONDA, 1702.00), 5 g of NaCl (sigma, S7653-5 kg), 34 μg/ml of chloramphenicol (sigma, C0857))], 2% glucose (Sigma, G5400) and 5 mM $MgCl_2$ (sigma, M2393) at 37° C. for 2-3 hrs ($OD_{600}$=0.5~0.7). Thereafter, the cells were infected with helper phage, followed by culture in a medium containing 2×YTCMK [2×YT CM, kanamycin (Sigma, K1876) 70 μg/ml, 1 mM IPTG (ELPISBIO, IPTG025)] at 30° C. for 16 hrs. The cells proceeded to centrifugation (4500 rpm, 15 min, 4° C.) and supernatant was obtained, which was dissolved in a solution supplemented with 4% PEG (Fluka 81253) 6000 and 3% NaCl (Sigma 57653), followed by reaction in ice for 1 hr. The reactant was centrifuged again (8000 rpm, 20 min, 4° C.). The pellet was dissolved in PBS, which proceeded to centrifugation again (12000 rpm, 10 min, 4° C.) As a result, the supernatant containing library phage was obtained, which was transferred into a new tube and stored at 4° C.

Example 3

Panning by Phage Display

When VCAM-1 consisting of seven IgG-like domains binds with its ligand, alpha4beta1 integrin (α4β1 integrin), its domains 1 and 4 are known to function as a binding motif. Thus, panning was performed using human VCAM-1-D1-D4 (hVCAM-1-D1-D4) as well as the entire VCAM-1 molecule. In this Example, the panning method and result for hVCAM-1-D1-D4 will be described.

<3-1> Panning on hVCAM-1-D1-D4

An IMMUNO tube (Nunc 470319) was coated with 30 μg of hVACM1-D1-D-His antigen using 4 ml of coating buffer [coating buffer; 1.59 g of $Na_2CO_3$(sigma, S7795), 2.93 g of $NaHCO_3$(sigma, S8875), 0.2 g of $NaN_3$(sigma, S2002)] at 4° C. for 16 hrs with a rotator. Then, the antigen was dissolved in PBS at room temperature for 2 hrs, followed by blocking in the IMMUNO tube using skim milk [(BD, 232100)-4% in 1×PBS]. 2 ml of the prepared library phage was added to the IMMUNO tube, followed by reaction at room temperature for 2 hrs. The IMMUNO tube was washed 5 times with PBST (0.05%) and twice with PBS. After washing, antigen specific scFV-phage was eluted using 100 mM TEA (Sigma T-0886). E. coli (XL1-Blue, stratagene, 200249) was transfected with the eluted phage, followed by amplification. The phage amplified in the first round of panning was washed 13 times with PBST and 23 times with PBS, followed by the second-third rounds of panning by the same manner as described above except that washing times were increased. In order to screen the antibodies having cross-reactivity to mouse VCAM-1 using the phage antibody of $3^{rd}$ polyclonal phage antibodies, the forth round of panning was performed using mVCAM-1-His as an antigen. As a result, the number of phage antibody binding to mVCAM-1-His did not increase. However, since the phage antibodies having a binding capacity to hVCAM-1-D1-4 were subjected to the fourth round of panning using the mVCAM-1-His antigen, it can be seen that the resulting phage antibodies had cross-reactivity. Further, the phage antibodies from the forth round of panning were subjected to the fifth round of panning. As a result, colony titer of phage against the mVCAM-1-His antigen increased at least 10 times (Table 1 and FIG. 1).

TABLE 1

| Result of Panning by hVCAM-1-D1-4 antigen and mVCAM-1-His antigen | | | |
|---|---|---|---|
| Target Antigen | Panning round | Initial number of phage | Number of binding phage |
| hVCAM-1-D1-4 | $1^{st}$ | $2.5 \times 10^{13}$ | $8.1 \times 10^5$ |
|  | $2^{nd}$ | $1.4 \times 10^{13}$ | $1.0 \times 10^6$ |
|  | $3^{rd}$ | $1.8 \times 10^{13}$ | $2.4 \times 10^8$ |
| mVCAM-1-his | $4^{th}$ | $2.1 \times 10^{13}$ | $2.4 \times 10^7$ |
| mVCAM-1-his | $5^{th}$ | $9 \times 10^{12}$ | $5 \times 10^8$ |

<3-2> Result of Panning on hVCAM-1-D1-D4 and mVCAM-1

Cell stocks obtained from the $1^{st}$-$5^{th}$ pannings and stored as frozen were dissolved in a medium containing 5 ml of 2×YTCM, 2% glucose, and 5 mM $MgCl_2$ to $OD_{600}$=0.1. Thereafter, the cells were cultured at 37° C. for 2-3 hrs ($OD_{600}$=0.5~0.7), which were infected with M1 helper phage. Thereafter, the cells were cultured in a medium containing 2×YTCMK, 5 mM $MgCl_2$, and 1 mM IPTG at 30° C. for 16 hrs. The cultured cells were centrifuged (4500 rpm, 15 min, 4° C.), and the supernatant was transferred into a new tube ($1^{st}$~$3^{rd}$ panning poly scFv-phage). A 96-well IMMUNO-plate (NUNC 439454) was coated with VCAM-1 antigen (100 ng/well) using a coating buffer at 4° C. for 16 hrs, followed by blocking with skim milk dissolved in PBS (4%). Each well was washed with 0.2 ml of PBS-tween20 (0.05%). 100 µl of the $1^{st}$-$3^{rd}$ panning poly scFV-phage was added to each well, followed by reaction at room temperature for 2 hrs. Each well was washed four times with 0.2 ml of PBS-tween20 (0.05%). The secondary antibody anti-M13-HRP (Amersham 27-9421-01) was diluted at 1:2000, followed by reaction at room temperature for 1 hr. After washing with 0.2 ml of PBS-tween20 (0.05%), OPD tablet (Sigma 8787-TAB) was added to a PC buffer [$C_6H_8O_7H_2O$ (sigma, C0706) 5.1 g, $Na_2HPO_4$ (sigma, S7907) 7.3 g] to prepare a substrate solution, which was added to each well by 100 µl/well, followed by color development for 10 min. $OD_{490}$ was measured by using a spectrophotometer (MolecularDevice, USA). As a result of polyPhage ELISA, binding capacity to hVCAM-1-D1-4 was found to reach saturation in the phage antibodies from the forth round of panning, and binding capacity to mVCAM-1 was found to reach saturation in the phage antibodies from the fifth round of panning. They also showed cross-reactivity with a strong affinity to hVCAM-1-D1-4 and mVCAM-1-His, compared to the control group (FIG. 1).

<3-3> Screening of Monoclonal Antibody

Colonies obtained from polyclonal antibodies (the $3^{rd}$ round of panning using the entire hVCAM-1 antigen and the $4^{th}$-$5^{th}$ rounds of panning using hVCAM-1-D1-D4 antigen) having a strong binding capacity were cultured in a 96-deep well plate (Bioneer, 90030) containing a medium supplemented with 2×YTCM, 2% glucose and 5 mM $MgCl_2$, 1 ml/well, at 37° C. for 16 hrs. The cells were cultured until $OD_{600}$ reached 0.1. 100-200 µl of the culture solution was inoculated in a medium supplemented with 2×YTCM, 2% glucose and 5 mM $MgCl_2$, which was loaded in a 96-deep well plate, followed by culture at 37° C. for 2-3 hrs until $OD_{600}$ reached 0.5-0.7. The cells were infected with M1 helper phage (MOI=1:20) and the infected cells were cultured in a medium supplemented with 2×YTCMK, 5 mM $MgCl_2$, and 1 mM IPTG at 30° C. for 16 hrs. The cultured cells were centrifuged (4500 rpm, 15 min, 4° C.) and the supernatant was obtained, to which 4% PEG 6000 and 3% NaCl were added. Upon completion of dissolving, reaction was induced in ice for 1 hr. The reactant was centrifuged (8000 rpm, 20 min, 4° C.) and the pellet was dissolved in PBS. Centrifugation (12000 rpm, 10 min, 4° C.) was performed again and the supernatant was obtained, from which the panning monoclonal scFv phages were obtained. The phage was transferred in a new tube and stored at 4° C.

Subsequently, a 96-well IMMUNO-plate was coated with hVCAM-1-Fc chimera (R&D Systems) (100 ng/well) at 4° C. for 16 hrs, followed by blocking with skim milk dissolved in PBS (4%). Each well of the 96-well IMMUNO-plate was washed with 0.2 ml of PBS-TWEEN 20 (0.05%). 100 µl of the $3^{rd}$ panning monoclonal scFV-phage (each 100 scFv-phage) was added to each well, followed by reaction at room temperature for 2 hrs. Each well was washed four times with 0.2 ml of PBS-tween 20 (0.05%). The secondary antibody anti-M13-HRP was diluted at 1:2000, followed by reaction at room temperature for 1 hr. Subsequently, the plate was washed with 0.2 ml of PBS-tween 20 (0.05%), followed by color development. $OD_{490}$ was measured.

As a result, binding capacities of 68 monoclones to various VCAM-1 antigens were compared, and their types were confirmed by finger printing and sequence analysis. Finally, 22 different types of phage antibodies were selected.

Example 4

Cloning of Full IgG Form

To convert the monoclonal phage antibodies against hVCAM-1 from phage to full IgG vector, colony PCR (iCycler iQ, BIO-RAD) was performed to obtain a heavy chain using 1 µl of monoclonal DNA and 10 pmole/µl of a heavy chain forward primer (TTGGTGGCCACAGCGGCCGAT-GTCCACTCGCAGATGCAGCTGGTGCAGTC, SEQ ID NO. 29) and a heavy chain reverse primer (GAGGAG-GCTAGCTGAGGAGACGGTGA, SEQ ID NO. 30) for 4B PCR, a heavy chain forward primer (TTGGTGGCCA-CAGCGGCCGATGTCCACTCGCAGGTG-CAGCTGGTGGAGTC, SEQ ID NO. 31) and a heavy chain reverse primer (SEQ ID NO. 30) for 7C PCR, and a heavy chain forward primer (SEQ ID NO. 29) and a heavy chain reverse primer (SEQ ID NO. 30) for 7H PCR, 5 µl of 10× buffer, 1 µl of 10 mM dNTP mix, 0.5 µl of pfu DNA polymerase (Solgent, co., 2.5 U/µl), and distilled water. Colony PCR was also performed to obtain a light chain using a light chain forward primer (TTGGTGGCCACAGCGGCCGAT-GTCCACTCGCAGCCTGTGCTGACTCAGCC, SEQ ID NO. 32) and a light chain reverse primer (GAG-GAGAGATCTTTAGGACGGTGACCTTGGTCCC, SEQ ID NO. 33) for 4B PCR, a light chain forward primer (TTG-GTGGCCACAGCGGCCGATGTCCACTCG-CAGCCTGTGCTGACTCAATC, SEQ ID NO. 34) and a light chain reverse primer (GAGGAGAGATCTTTAG-GACGGTCAGCTTGGTCCC, SEQ ID NO. 35) for 7C PCR, and a light chain forward primer (TTGGTGGCCACAGCG-GCCGATGTCCACTCGGACATCCAGAT-GACCCAGTCTCC, SEQ ID NO. 36) and a light chain reverse primer (GAGGAGAGATCTTTTGATCTC-CACTTTGGT, SEQ ID NO. 37) for 7H PCR in the same manner. PCR was performed under the following conditions: at 94° C. for 1 min, at 55° C. for 1 min, and at 72° C. for 1 min for 30 cycles.

The heavy chain DNAs obtained from PCR were eluted by using a DNA-gel elution kit (Qiagen, MD), and mixed with 1 µl of pNATAB H vector (10 ng), 15 µl of heavy chain (100~200 ng), 2 µl of 10× Buffer, 1 µl of ligase (1 U/µl), and distilled water, left at room temperature for 1-2 hrs for ligation with the vector. Competent cells (XL1-blue) were added thereto, and left in ice for 30 min, followed by heat-shock at 42° C. for 90 sec for transformation. The mixture was placed in ice again for 5 min, and 1 ml of LB medium was added thereto. After incubation at 37° C. for 1 hr, the cells were spread on LB Amp solid medium, followed by incubation at 37° C. for 16 hrs. The single colony obtained was inoculated in 5 ml of an LB Amp liquid medium, followed by incubation at 37° C. for 16 hrs. DNA was extracted from the culture medium using a DNA-prep. Kit (Nuclogen). The light chain DNA was also extracted using a pNATAB L vector in the same manner as the above. Sequencing analysis of the obtained DNA was performed using a CMV-proF primer (AAA TGG GCG GTA GGC GTG, SEQ ID NO. 38) (Solgent, Korea). As a result, it was confirmed that the heavy chain and the light chain sequences of full IgG converted from 22 clones against VCAM-1 were identical to the sequence of phage antibody.

Example 5

Transient Gene Expression of Antibody

Transient gene expression of antibody gene from the cloned full IgG heavy chain DNA and light chain DNA was performed.

CHO (Chinese Hamster Ovary)-S was used as a host cell for transient gene expression to induce transfection in a mixed solution of OPTI-MEM (GIBCO 31985, Invitrogen) with LIPOFECTAMINE 2000 (Cat no. 11668-019, Invitrogen) and DNA (1:1). To maximize the transient expression, heavy chain DNA and light chain DNA were used at a ratio of 1:1. RPMI 1640 medium (GIBCO 22400, Invitrogen) was used for transfection, and the cell was used at a concentration of $2 \times 10^6$ cells/ml. After the mixed solution was reacted for 20 min, and mixed with the transfection medium at a ratio of 1:9, followed by incubation in a 5% $CO_2$ 37° C. shaking incubator at 110 rpm for 4 hrs. Subsequently, CD-CHO medium (GIBCO 10743, Invitrogen) containing 8 mM glutamine (GIBCO 25030, L-Glutamine 200 mM, 100×, Invitrogen) and HTS (GIBCO, HT Supplement, Cat no. 11067-030, Invitrogen) was added thereto in an equal volume to that of the transfection medium. The flask was incubated in an 8% $CO_2$ 37° C. shaking incubator at 100 rpm for 4 days. The cultured sample was centrifuged at 8,000 g for 15 min to remove cell debris, and the supernatant was filtered using a 0.22 μm filter (Corning) to prepare a culture solution for isolation and purification of antibody.

Example 6

Isolation and Purification of Antibody

The supernatant prepared in Example 5 was passed through a recombinant protein-A sepharose column (Hitrap rProteinA FF, 5 mL, GE healthcare) equilibrated using an equilibrium buffer (50 mM Tris-HCl (pH 7.4), 100 mM NaCl). The antibodies binding to the column were eluted with 0.1 M Na-citrate (pH 3.0), 100 mM NaCl solution, and neutralized with 1 M Tris-HCl (pH 9.0), followed by dialysis in a PBS (phosphate buffered saline, pH 7.4, Welgene) buffer solution. The purified antibody was electrophoresed on Bis-Tris 4-12% gradient SDS-polyacrylamide gel (NUPAGE gel, Invitrogen) under reduced conditions. As a result, about 55 kDa of heavy chain and about 25 kDa of light chain were detected.

Example 7

Analysis of Affinity of Antibody to Antigen

<7-1> Affinity to Antigen Domain

The antibodies isolated and purified in Example 6 were designated as 4B, 7C and 7H, respectively. It was confirmed that they contain a heavy chain as defined by SEQ ID NO. 1 and a light chain as defined by SEQ ID NO. 13 (4B), a heavy chain as defined by SEQ ID NO. 5 and a light chain as defined by SEQ ID NO. 17 (7C), and a heavy chain as defined by SEQ ID NO. 9 and a light chain as defined by SEQ ID NO. 21 (7H), respectively. The affinity of the isolated antibodies to antigen was analyzed as follows.

The location of anti VCAM-1 antibody-binding regions in VCAM-1 consisting of seven domains was identified by ELISA. Each well of a microplate was coated with a recombinant human VCAM-1 domain 1~2/Fc chimera (herein below, referred to as 'VD2', A&R therapeutics), VCAM-1 domain 1~4/Fc chimera (herein below, referred to as 'VD4', A&R therapeutics), and VCAM-1 domain 1~7/Fc chimera (herein below, referred to as 'VD7', R&D, 862-VC) at a concentration of 2 g/ml at 4° C. overnight. The plate was washed using PBS once, and blocked using PBS supplemented with 3% BSA (bovine serum albumin) at 37° C. for 2 hrs, followed by incubation in cell culture medium containing antibody (1:50) at 37° C. for 2 hrs. The plate was washed with PBS containing 0.05% TWEEN 20 four times, and the amount of anti VCAM-1 antibody binding to recombinant human VCAM-1 antigen was detected by anti-Fab monoclonal antibody horseradish peroxidase-conjugated anti-F (ab')2 antibody. The plate was reacted with a TMB substrate solution (3,3,5,5-Tetramethylbenzidine) at room temperature for about 5 min, and the reaction was terminated by 1 N (normal)) sulfuric acid solution to measure optical density at 450 nm.

As shown in FIG. 3, it was found that 4B and 7H had a strong binding capacity to VD2 having only 1-2 of VCAM-1 domains, whereas 7C has very little binding capacity to VD2 and a binding capacity to VD4 and VD7. That is, 4B and 7H bind to the domain 1-2 and 7C binds to the domain 3~4, among seven domains of VCAM-1.

<7-2> Affinity Analysis by BIACORE

In order to determine the binding affinity of anti VCAM-1 antibodies 4B, 7C and 7H to human and mouse VCAM-1 antigen, each antigen as a ligand was immobilized to a sensor chip (Sensor chip CM5, BIACORE, BR-1003-99), and then each dilution of the human antibodies was applied to the immobilized ligand using BIACORE to induce association and dissociation between antigen and antibody, thereby determining the association/dissociation constant $K_D$ value, which indicates a binding interaction between the corresponding antigen and antibody. The results are shown in FIG. 1 (Reference: Thomas Hofer, Wisit Tangkeangsirisin, Michael G. Kennedy, Rose G. Mage, Stephen J. Raiker, Karthik Venkatesh, Hakjoo Lee, Roman J. Giger, Christoph Rader Chimeric rabbit/human Fab and IgG specific for members of the Nogo-66 receptor family selected for species cross-reactivity with an improved phage display vector Journal of Immunological Methods 318 (2007) 75.87; Paula Gomes a, David Andreu Direct kinetic assay of interactions between small peptides and immobilized antibodies using a surface plasmon resonance biosensor Journal of Immunological Methods 259, 2002.217-230, and Kikuchi Y, Uno S, Nanami M, Yoshimura Y, Iida S, Fukushima N, Tsuchiya M. Determination of concentration and binding affinity of antibody fragments by use of surface plasmon resonance. Journal of Bioscience and Bioengineering Vol. 100, No. 3, 311-317, 2005).

BIACORE analysis comprises the three steps of 1)

Pre-concentration that determines coupling conditions between sensor chip and ligand; 2) immobilization of ligand to sensor chip; and 3) binding of analyte to the immobilized ligand.

1) Pre-concentration

In this experiment, a conventional BIACORE sensor chip CM5 (BIACORE, BR-1003-99) was used, and before ligand immobilization to the chip, the electrostatic attraction of the ligand to the sensor surface was determined via change in pH 4.0 5.5 of sodium acetate, which is used as a coupling buffer.

2) Ligand Immobilization

For ligand immobilization to the sensor chip CM5, the chip should be first activated with a mixture of N-hydroxysuccinimide (NHS) and N-ethyl-n'-(dimethylaminopropyl) (EDC) (Amine Coupling Kit, BR-1000-50) to prepare a NHS-ester-activated chip surface being highly reactive to an amino group. 1 mg/ml of ligand to be immobilized was diluted in 97 µl of each sodium acetate solution (varying within the pH range from 4.0 to 5.5) at a dilution ratio of 3/100, and then applied at a flow rate of 10 µl/min for about 3 min (as a negative control, the ligand was diluted using a running buffer, HBS-EP buffer (BIACORE AB, Sweden) in the same manner). In order to immobilize the ligand at a predetermined value target RU (resonance unit), serial injection was carried out automatically, until reaching target RU. The ligand-immobilized chip was inactivated by injection of 1 M ethanolamine (Amine Coupling Kit, BR-1000-50) at a flow rate of 10 µl/min for about 3 min. The final RU was determined by an immobilization report which provides a difference in RU values before and after injection of ethanolamine.

3) Binding of Analyte to the Immobilized Ligand

A flow cell2-flow cell mode provided by BIACORE instrument was employed in this experiment in order to remove non-specific binding. At this time, a recombinant VCAM1/Fc antigen was immobilized as a ligand to the flow cell2, and BSA (Bovine Serum Albumin) was immobilized to the flow cell. Then, each of the anti VCAM-1 antibodies 4B, 7C and 7H as the analyte were applied to flow cell 1 and 2, simultaneously. The sensogram RU of flow cell was automatically subtracted from the sensogram RU of flow cell2. Subsequently, the analytes were applied at a flow rate of 30 µl/min for about 3 min, and then dissociation was induced for 120 sec. Through this procedure, an association/dissociation curve of the corresponding antigen and antibody was obtained, and an association/dissociation constant $K_D$ was calculated by BIAevaluation program (BIACOREAB, Sweden), as shown in the following Table 2.

TABLE 2

| Antibody | Human VCAM-1 antigen $K_D$(nM) | Mouse VCAM-1 antigen $K_D$(nM) |
|---|---|---|
| 4B | 0.5 | — |
| 7C | 38.8 | 36.9 |
| 7H | 5.44 | 10.7 |

The above Table 2 represents the binding capacity or affinity of human and mouse VCAM-1 antigen-specific anti VCAM-1 human monoclonal antibodies to antigen, and a protein affinity analyzer, BIACORE (BIACORE AB, Sweden) was used to analyze a species specific antigen-antibody affinity to the biologically different species, human and mouse antigens. The affinity constant $K_D$ value of corresponding antigen-antibody was calculated in a 1:1 binding mode.

As a result, all 4B, 7C and 7H were found to have an excellent binding capacity to the human antigen, and of them, the antibody 4B was found to have an excellent binding capacity of about 1 nM. In addition, the antibodies 7C and 7H, except 4B, were found to have a binding capacity to the mouse antigen of about 10100 nM.

Example 8

Inhibitory Effect of Antibody on Leukocyte Adhesion

<8-1> Inhibitory Effect on Adhesion between Human VCAM-1 Antigen and Leukocyte

Each well of 96-well plate (MAXISORP, Nunc) was coated with 100 µl of recombinant human VCAM-1 (10 µg/ml, Cat. No.: 809-VR-200, R&D systems) for 1 hr, and then human antibodies 4B, 7C and 7H were added to the VCAM-1-coated well in an amount of 0.01, 0.1, 1.0 and 10.0 µg for antigen binding for 1 hr. At this time, 1.0 and 10.0 µg of 4B2 mouse anti-human VCAM-1 monoclonal antibody (Cat. No.: BBA5, R&D Systems) was used as a positive control, and as a negative control, the antigen was only treated without antibody. While binding of antibodies to the antigen, the fluorescence staining of human leukocyte cell U937 (Cat. No.: CRL-1593.2, ATCC) was performed using 5 µM of BCECF-AM (Cat. No.: 216254, Calbiochem). Next, U937 cell was treated with 100% human serum (Cat. No.: H4522, Sigma) to inactivate the Fc receptor on the cell surface. The leukocyte cells treated with fluorescence staining and Fc receptor inactivation were suspended in RPMI 1640 (Cat. No.: 22400-089, Invitrogen) supplemented with 1% fetal calf serum to $1.0 \times 10^6$ cells/ml. 100 µl of the prepared U937 cells were applied to each well of the antigen and antibody-treated plate, and aluminum foil was used to block light. The plate was incubated in a 37° C. 5% $CO_2$ incubator for 15 min, and each well was filled with RPMI 1640 supplemented with 1% fetal calf serum, and sealed tightly with a sealing tape. The plate was placed upside down, and centrifuged at 200×g force for 5 min. The sealing tape was removed from the upside-down centrifuged plate. The medium and unbound U937 cells were completely removed, and 150 µl of cell lysis buffer (50 mM Tris-HCl (pH8.5), 0.1% SDS) was added to each well to lyse the bound U937 cells for 15 min. Subsequently, the plate was placed in a fluorometer (GEMINI X, Molecular Devices), and fluorescence intensity was measured at an absorbance wavelength 485 nm/emission wavelength 530 nm. Mean values of the triplicate measurements (per each experimental condition) were calculated, and reduction in fluorescence intensity compared to that of non-antibody treated group was calculated to analyze the inhibition rate. As a result, 4B showed 80% inhibition at an amount of 0.1 µg or more. 7C and 7H showed a weak inhibitory effect at a lower amount (0.01-1.0 µg), but 90% inhibition at an amount of 10 µg (FIG. 4).

<8-2> Inhibitory Effect on Adhesion between Human Endothelial Cell and Leukocyte $2 \times 10^4$ human endothelial cell HUVEC was plated on each well of a 96-well plate (MICROTEST tissue culture 96-well plate, BD Falcon), and cultured in EGM-2 media (Lonza) for about 3 days according to the manufacturer's instructions. When the cell monolayer was observed under a microscope, the cells were stimulated with 20 ng/ml of human TNF-α for 24 hrs. Thereafter, to remove TNF-α, each well was washed with 200 µl of EGM-2 medium twice, and the human antibodies 4B, 7C and 7H were added to the HUVEC monolayer plated on the well in an amount of 0.01, 0.1, 1.0 and 10.0 µg, respectively. The plate was incubated for 1 hr to induce antigen-antibody binding. At this time, 1.0 and 10.0 µg of 4B2 mouse anti-human VCAM-1 monoclonal antibody (Cat. No.: BBA5, R&D) and mouse anti-α4 integrin antibody were used as a positive control, and as a negative control, the antigen was only treated without antibody. While binding of antibodies to the antigen, the fluorescence staining of human leukocyte cell U937 (Cat. No.: CRL-1593.2, ATCC) was performed using 5 µM of BCECF-AM (Cat. No.: 216254, Calbiochem). Next, U937 cell was treated with 100% human serum (Cat. No.: H4522, Sigma) to inactivate the Fc receptor on the cell surface. The U937 cells treated with fluorescence staining and Fc receptor inactivation were suspended in RPMI 1640 (Cat. No.: 22400-089, Invitrogen) supplemented with 1% fetal calf serum to $1.0 \times 10^6$ cells/ml. 100 µl of the prepared U937 cells were applied to each well of the antibody-treated HUVEC, and aluminum foil was used to block light. The plate was incubated in a 37° C. 5% $CO_2$ incubator for 10 min, and placed upside down to remove the medium and unbound cells. Each well was filled with RPMI 1640 supplemented with 1% fetal bovine serum, and sealed tightly with a sealing tape. The upside-down plate was centrifuged at 400×g force for 5 min. The sealing tape was removed from the upside-down centrifuged plate. The medium and unbound U937 cells were completely removed, and 150 µl of cell lysis buffer (50 mM Tris-HCl (pH8.5), 0.1% SDS) was added to each well to lyse the bound U937 cells for 15 min. Subsequently, the plate was placed in a fluorometer (GEMINI X, Molecular Devices), and fluorescence intensity was measured at an absorbance wavelength 485 nm/emission wavelength 530 nm. Mean values of the triplicate measurements (per each experimental condition) were calculated, and reduction in fluorescence intensity compared to that of non-antibody treated group was calculated to analyze the inhibition rate. As a result, 4B showed about 50-60% inhibition at an amount of 0.1 µg~10.0 µg. 7C and 7H showed a weak inhibitory effect at a lower amount (0.01-1.0 µg), and 50-60% inhibition at an amount of 10 µg (FIG. 5). These results are similar to the analysis results of inhibitory effect on adhesion between VCAM-1 antigen and leukocyte in Example <8-1>.

Example 9

Inhibitory Effect of Antibody on RhoA (Ras Homolog Gene Family, Member A) and ROS (Reactive Oxygen Species) Activity <9-1> Inhibitory Effect on RhoA (Ras Homolog Gene Family, Member A) Activity $2 \times 10^4$ HUVEC (Human Umbilical Vein Endothelial Cells) were inoculated in a 6-well plate, and cultured to confluency for about 3 days. To remove serum present in the culture medium, the plate was washed with EBM-2 medium (Cat. No.: CC-3156, Lonza) once, and 20 ng/ml of human TNF-α diluted in EBM-2 medium supplemented with 0.25% fetal bovine serum was added to stimulate the cells overnight (about 14~16 hrs). After removing the culture medium, anti VCAM-1 antibody and control antibody were added at a concentration of 10 µg/ml, followed by reaction for 30 min at 37° C. 10 µg/ml of anti VCAM-1 antibody (Cat. No.: BBA5, BD) used for cross-linking of VCAM-1 on the cell surface was added, followed by reaction for 30 min at 37° C. HRP-conjugated anti-mouse antibody (Cat. No.: A9917, Sigma) was added in a ratio of 1:100, followed by reaction for 15 min at 37° C. After the reaction was completed, the plate was immediately placed in ice to remove the medium, and washed with cold PBS once. After the residual PBS was completely removed from the plate, 100 µl of a cell lysis buffer included in a RhoA activation kit (Cat. No.: BK124, Cytoskeleton) was added to each well, and the lysed cells were recovered. Subsequent procedures were carried out according to the manual in the kit, and repeated three times.

Figure 6:
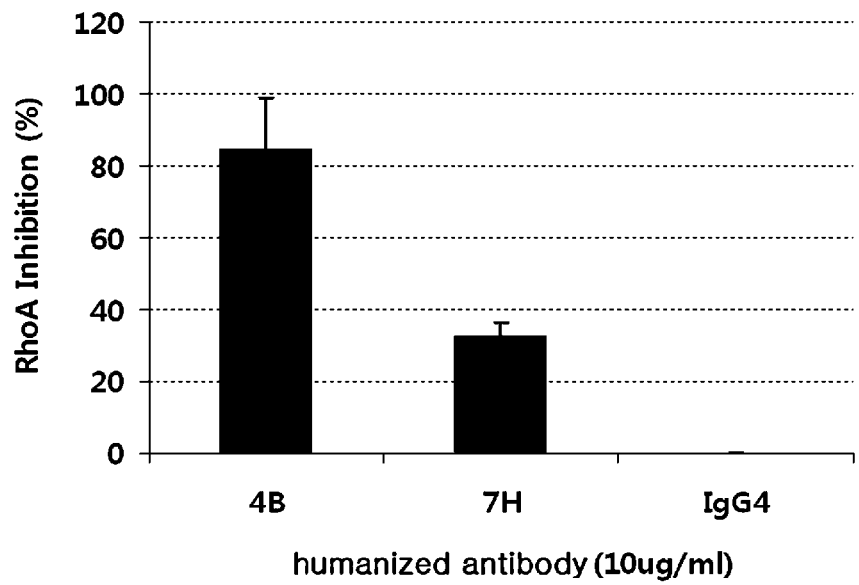
FIG. 6 is the result of analyzing the inhibitory activity of anti VCAM-1 human monoclonal antibodies on RhoA (Ras homolog gene family, member A) activity.

As a result, it was found that the antibodies 4B and 7H showed about 80% and 30% inhibition rate on the RhoA activity which was induced by cross-linking of VCAM-1 expressed on the cell surface (FIG. 6).

<9-2> Inhibitory Effect on ROS (Reactive Oxygen Species) Activity $2 \times 10^4$ HUVEC (Human Umbilical Vein Endothelial Cells) were inoculated in a 6-well plate, and cultured to confluency for about 3 days. To remove serum present in the culture medium, the plate was washed with EBM-2 medium (Cat. No.: CC-3156, Lonza) once, and 20 ng/ml of human TNF-α diluted in EBM-2 medium supplemented with 0.25% fetal bovine serum was added to stimulate the cells overnight (about 14~16 hrs). After removing the culture medium and washing with EBM-2 medium twice, anti VCAM-1 antibody and control antibody were added at a concentration of 10 µg/ml, followed by reaction for 30 min at 37° C. After each well was washed with EBM-2 medium twice, 10 µg/ml of anti VCAM-1 antibody (Cat. No.: BBA5, BD) used for cross-linking of VCAM-1 on the cell surface was added, followed by reaction for 30 min at 37° C. After each well was washed with EBM-2 medium twice, HRP-conjugated anti-mouse antibody (Cat. No.: A9917, Sigma) was added in a ratio of 1:100, followed by reaction for 30 min at 37° C. Each well was washed with EBM-2 medium twice. After the medium was completely removed, each well was treated with 150 µl of 10 µM DCF (2',7'-dichlorofluorescein diacetate) diluted in EBM-2 medium. Then, fluorescence (wavelength 495 nm~527 nm) was examined every 10 min for 3 hrs, and the effect of the antibody was evaluated by the value measured at 3 hrs. The experiment was repeated three times.

Figure 7:
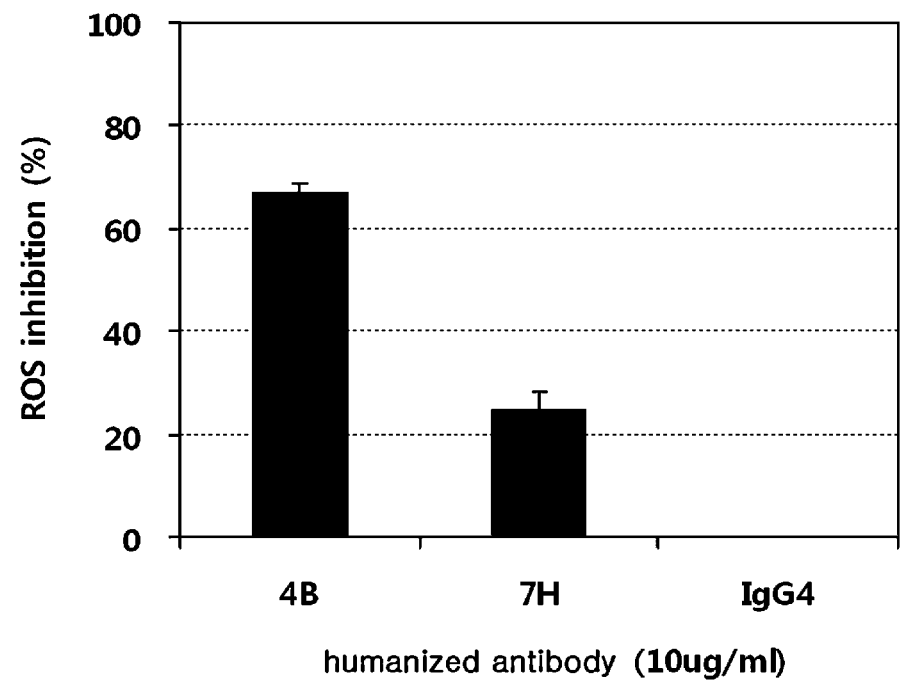
FIG. 7 is the result of analyzing the inhibitory activity of anti VCAM-1 human monoclonal antibodies on ROS (Reactive oxygen species) activity.

As a result, it was found that the antibodies 4B and 7H showed about 65% and 25% inhibition rate on the ROS activity which was induced by cross-linking of VCAM-1 expressed on the cell surface (FIG. 7).

The above results suggest that the antibodies according to the present invention significantly inhibit RhoA and ROS activity; that is, when immune cells bind to endothelial cells, the gap between endothelial cells is enlarged to form a hole, and immune cells pass through the hole, and migrate into the inflamed site by endothelial cell signal transduction. However, the antibodies according to the present invention significantly inhibit the ROS and RhoA activity in the above endothelial cell signaling pathway, so that the gap formation between endothelial cells is inhibited not to form a hole. Consequently, migration of immune cells into the inflamed site is prevented.

Example 10

Pharmacokinetics Analysis

In this Example, pharmacokinetics analysis was performed by comparing in vivo half life between anti VCAM-1 chimeric monoclonal antibody (Korean Patent Application No. 10-2007-0053526, "VCAM-1 specific monoclonal antibody") applied for by the present inventors and the human monoclonal antibodies of the present invention. That is, a seven-week old BALB/c mouse (female, Orient) was intraperitoneally administered with 500 µg of anti VCAM-1 chimeric monoclonal antibody and the human antibodies 4B and 7C, respectively. Before administration and on 30 min, 1, 2, 4, 8, 12, 24, 36, 48, 60, 72 and 96 hrs after administration, blood samples were collected from the tail vein. ELISA was performed to determine serum IgG level and half life (the time required for the concentration to decrease by ½ of maximum blood concentration), and the results are shown in the following Table 3.

TABLE 3

| Anti VCAM-1 chimeric monoclonal antibody | 4B | 7C |
|---|---|---|
| Half life (hr) | 31.0 | 88.9 | 89.5 |

With reference to Table 3, the in vivo half life of 4B and 7C was found to be about 89 hrs, which increased about 3 times more than that of anti VCAM-1 chimeric monoclonal antibody.

Example 11

Efficacy Test on Mouse Asthma

<11-1> Establishment of Asthma Animal Model

In order to confirm in vivo efficacy of the human antibodies 7C and 7H specific to mouse VCAM-1 antigen, an asthma animal model was established. A 6 week-old female BALB/c mouse (Orient) was intraperitoneally administered with a mixture of 75 μg of ovalbumin (Sigma, A5503) and 2 mg of alum as an adjuvant (Pierce, 77161) on days 0, 2 and 7. For one week from day 14 to 20, topical sensitization of 2% ovalbumin was carried out using a nebulizer (Omron) for 30 min to induce asthma (Reference: S. J. Park, W. H. Shin, J. W. Seo, et al. Anthocyanins inhibit airway inflammation and hyperresponsiveness in a murine asthma model. Food and Chemical Toxicology 45 (2007) 1459-1467). The antibodies were intraperitoneally administered at a dose of 0.2 mg/mouse (8 mg/kg) and 0.05 mg/mouse (2 mg/kg) on day 14 once. As a control, aminophylline (Dae Won Pharm) was intraperitoneally administered at a dose of 10 mg/kg everyday from day 14 to 20 for comparison of therapeutic efficacy. On 21 day, anatomical patterns of inflammation were examined.

<11-2> Efficacy of Antibody in Asthma Animal Model 24 hrs after the last ovalbumin sensitization, the mouse was anesthetized with ether (Junsei), and fixed on a dissecting table. The chest was dissected to expose the trachea, followed by ligature and catheter placement. 1 ml and 0.8 ml of PBS was injected to perform bronchoalveolar lavage. The obtained bronchoalveolar lavage fluid was centrifuged at 4° C. and 2,000 rpm for 5 min. The cells were suspended in PBS to count the number of cell. 20,000 cells were subjected to CYTOSPIN (Thermo scientific) at 2,000 rpm for 3 min, and spread on a slide, followed by DiffQuick staining. DiffQuick staining (Sysmex, 38721) was performed by dipping the slide in a solution I for 15 sec, in a solution II for 60 sec, and in a solution III for 40 sec, and washing the slide with tap water. The slide was air-dried overnight, and fixed using a mount solution (Fluka, 44581). 200 or more of inflammatory cells were examined under an optical microscope (×100), and divided into eosinophils, macrophages, neutrophils, and lymphocytes for comparison (Reference: D. Y. Kim, S. Y. Ryu, J. E. Lim, et al. Anti-inflammatory mechanism of simvastatin in mouse allergic asthma model. European Journal of Pharmacology 557 (2007) 76-86).

As a result, when the anti VCAM-1 human antibody was administered at a dose of 0.2 mg/mouse, the total number of inflammatory cells was significantly reduced. In particular, the number of lymphocyte and eosinophil was found to be reduced in the group treated with 7H at a dose of 0.05 mg/mouse and 0.2 mg/mouse. When 7C was administered at a dose of 0.05 mg/mouse and 0.2 mg/mouse once, the total number of inflammatory cells was reduced, and in particular, the number of macrophage and eosinophil was significantly reduced. That is, the inhibitory effect of two antibodies on inflammatory cell influx in asthma was found to be similar to that of aminophylline which is currently used for the treatment of asthma (FIG. 8).

The invention claimed is:

1. A human monoclonal antibody, or an antigen binding fragment thereof, that specifically binds to human vascular cell adhesion molecule-1 (VCAM-1) to inhibit the interaction between leukocytes and activated endothelial cells wherein the human monoclonal antibody comprises:
  (a) a heavy chain variable region that contains a heavy chain CDR1 as defined by SEQ ID NO. 2; a heavy chain CDR2 as defined by SEQ ID NO. 3; and a heavy chain CDR3 as defined by SEQ ID NO. 4, and a light chain variable region that contains a light chain CDR1 as defined by SEQ ID NO. 14; a light chain CDR2 as defined by SEQ ID NO. 15; and a light chain CDR3 as defined by SEQ ID NO. 16;
  (b) a heavy chain variable region that contains a heavy chain CDR1 as defined by SEQ ID NO. 6; a heavy chain CDR2 as defined by SEQ ID NO. 7; and a heavy chain CDR3 as defined by SEQ ID NO. 8, and a light chain variable region that contains a light chain CDR1 as defined by SEQ ID NO. 18; a light chain CDR2 as defined by SEQ ID NO. 19; and a light chain CDR3 as defined by SEQ ID NO. 20;
  (c) a heavy chain variable region that contains a heavy chain CDR1 as defined by SEQ ID NO. 10; a heavy chain CDR2 as defined by SEQ ID NO. 11; and a heavy chain CDR3 as defined by SEQ ID NO. 12, and a light chain variable region that contains a light chain CDR1 as defined by SEQ ID NO. 22; a light chain CDR2 as defined by SEQ ID NO. 23; and a light chain CDR3 as defined by SEQ ID NO. 24; or
  (d) an antigen binding fragment of (a), (b), or (c).

2. The human monoclonal antibody according to claim 1, wherein the human monoclonal antibody of (b) or (c) further specifically binds to mouse vascular cell adhesion molecule-1 (VCAM-1).

3. The human monoclonal antibody according to claim 1, wherein the human monoclonal antibody of (a) comprises an amino acid sequence of heavy chain as defined by SEQ ID NO. 1 and an amino acid sequence of light chain as defined by SEQ ID NO. 13.

4. The human monoclonal antibody according to claim 3, wherein an association/dissociation constant ($K_D$ value) of the human monoclonal antibody to human VCAM-1 antigen is $1\times10^{-11}$ M to $9\times10^{-9}$ M.

5. The human monoclonal antibody according to claim 1, wherein the human monoclonal antibody of (b) comprises an amino acid sequence of heavy chain as defined by SEQ ID NO. 5 and an amino acid sequence of light chain as defined by SEQ ID NO. 17.

6. The human monoclonal antibody according to claim 5, wherein an association/dissociation constant ($K_D$ value) of the human monoclonal antibody to human and mouse VCAM-1 antigen is $1\times10^{-10}$ M to $9\times10^{-8}$ M.

7. The human monoclonal antibody according to claim 1, wherein the human monoclonal antibody of (c) comprises an amino acid sequence of heavy chain as defined by SEQ ID NO. 9 and an amino acid sequence of light chain as defined by SEQ ID NO. 21.

8. The human monoclonal antibody according to claim 7, wherein an association/dissociation constant ($K_D$ value) of the human monoclonal antibody to human and mouse VCAM-1 antigen is $1\times10^{-10}$ M to $9\times10^{-8}$ M.

9. The human monoclonal antibody according to claim 1, wherein the inhibition on the interaction between leukocytes and activated endothelial cells is performed by inhibiting the leukocyte adhesion to activated endothelial cells or preventing gap formation between endothelial cells due to reduction of ROS (Reactive oxygen species) and RhoA (Ras homolog gene family, member A) activity.

10. A composition comprising the human monoclonal antibody of claim 1.

11. The composition according to claim 10, wherein the human monoclonal antibody of (b) or (c) further specifically binds to mouse vascular cell adhesion molecule-1 (VCAM-1).

12. A method for detecting an antigen-antibody reaction between VCAM-1 in a biological sample of a subject suspected of having inflammatory disease or cancer, comprising providing a biological sample and the human monoclonal antibody of claim 1 and subsequently measuring the binding of the antibody and VCAM-1.

13. The method according to claim 12, wherein the human monoclonal antibody of (b) or (c) further specifically binds to mouse vascular cell adhesion molecule-1 (VCAM-1).

14. A composition comprising the human monoclonal antibody of claim 1 and a pharmaceutically acceptable carrier.

15. The composition according to claim 14, wherein the human monoclonal antibody of (b) or (c) further specifically binds to mouse vascular cell adhesion molecule-1 (VCAM-1).

16. A method for treating for inhibiting the interaction between leukocytes and activated endothelial cells, comprising the step of administrating a composition comprising the human monoclonal antibody of claim 1 to a subject.

17. The method according to claim 16, wherein the human monoclonal antibody of (b) or (c) further specifically binds to mouse vascular cell adhesion molecule-1 (VCAM-1).

* * * * *